(12) United States Patent
Goodbread

(10) Patent No.: US 9,995,666 B2
(45) Date of Patent: Jun. 12, 2018

(54) RESONANT SENSORS FOR FLUID PROPERTIES MEASUREMENT

(71) Applicant: Joseph H. Goodbread, Winterthur (CH)

(72) Inventor: Joseph H. Goodbread, Winterthur (CH)

(73) Assignee: RHEONICS GMBH, Winterthur (CH)

( * ) Notice: Subject to any disclaimer, the term of this patent is extended or adjusted under 35 U.S.C. 154(b) by 493 days.

(21) Appl. No.: 14/549,507

(22) Filed: Nov. 20, 2014

(65) Prior Publication Data

US 2015/0082873 A1 Mar. 26, 2015

Related U.S. Application Data

(63) Continuation-in-part of application No. PCT/US2013/066249, filed on Oct. 22, 2013.

(60) Provisional application No. 61/906,992, filed on Nov. 21, 2013, provisional application No. 61/717,029, filed on Oct. 22, 2012.

(51) Int. Cl.
*G01N 11/16* (2006.01)
*G01N 9/00* (2006.01)
*G01N 11/00* (2006.01)

(52) U.S. Cl.
CPC .............. *G01N 11/16* (2013.01); *G01N 9/002* (2013.01); *G01N 2009/006* (2013.01); *G01N 2011/0086* (2013.01)

(58) Field of Classification Search
CPC ... G01N 9/002; G01N 11/16; G01N 2009/006
See application file for complete search history.

(56) References Cited

U.S. PATENT DOCUMENTS

| 3,935,726 A | 2/1976 | Heinz |
| 4,135,826 A | 1/1979 | Holm |
| 4,655,075 A | 4/1987 | Albert et al. |
| 5,596,139 A | 1/1997 | Miura et al. |
| 5,837,885 A | 11/1998 | Goodbread et al. |
| 6,494,079 B1 | 12/2002 | Matsiev et al. |

(Continued)

FOREIGN PATENT DOCUMENTS

| JP | 03146847 A | 6/1991 |
| JP | 07072063 A | 3/1995 |

OTHER PUBLICATIONS

Agoston, Evaluation of a vibrating micromachined cantilever sensor for measuring the viscosity of complex organic liquids, Sciencedirect.com, Elsevier, Sensors and Actuators, 2005, Vienna, Austria.

(Continued)

*Primary Examiner* — R. A. Smith
*Assistant Examiner* — John M Royston
(74) *Attorney, Agent, or Firm* — Timothy E. Siegel Patent Law, PLLC; Timothy E. Siegel

(57) ABSTRACT

A resonator that includes an elastic tube defining an interior surface and a conductor threaded through the elastic tube. Solid material fills space between the conductor and the elastic tube interior surface, such that motion of the conductor is directly transferred to the elastic tube. In a preferred embodiment, the elastic tube is electrically conductive and said solid material insulates said conductor from said elastic tube.

11 Claims, 24 Drawing Sheets

(56) References Cited

U.S. PATENT DOCUMENTS

| | | | | |
|---|---|---|---|---|
| 6,917,887 B2* | 7/2005 | Henry | ............... | G01F 1/8404 |
| | | | | 702/45 |
| 7,434,457 B2 | 10/2008 | Goodwin et al. | | |
| 8,291,750 B1 | 10/2012 | Goodbread et al. | | |
| 8,752,416 B2 | 6/2014 | Goodbread et al. | | |
| 2009/0049928 A1* | 2/2009 | Hays | ............... | G01F 1/8413 |
| | | | | 73/861.356 |
| 2010/0000334 A1* | 1/2010 | Katsurada | ......... | G01F 1/8422 |
| | | | | 73/861.357 |
| 2011/0000315 A1* | 1/2011 | Tsubota | ............ | G01F 1/8418 |
| | | | | 73/861.357 |
| 2012/0186363 A1* | 7/2012 | Egner | ............... | G01F 1/8477 |
| | | | | 73/861.357 |

OTHER PUBLICATIONS

Goodwin, A Vibrating Edge Supported Plate, Fabricated by the Methods of Micro Electro Mechanical System for the Simultaneous Measurement of Density and Viscosity: Results for Methylbenzene and Octane at Temperatures between (323 and 423) K and Pressures in the Range (0.1 to 68) MPa, Journal of Chemical and Engineering Data, 2006, vol. 51, No. 1, U.S.

Requa, Electromechanically driven and sensed parametric resonance in silicon microcantilevers, Applied Physics Letters, 2006, vol. 88, Issue 26, CA, U.S.

\* cited by examiner

RESONANT SENSORS FOR FLUID PROPERTIES MEASUREMENT

RELATED APPLICATIONS

This application claims priority from U.S. Provisional Patent Application No. 61/906,992 filed Nov. 21, 2013, under 35 U.S.C. § 119. This application is also a continuation-in-part of Patent Cooperation Treaty Application No. PCT/US2013/066249, filed on Oct. 22, 2013, which claims priority from U.S. Provisional Patent Application No. 61/717,029, filed on Oct. 22, 2012, under 35 U.S.C. § 119. The entire contents of each of these applications are incorporated by reference as if fully set forth herein.

BACKGROUND

This application relates to devices for measuring the properties, such as density and viscosity, of fluids and compliant solids. More particularly, it relates to the construction of such devices that are hermetically sealed against corrosive and/or conductive fluids, which could otherwise degrade the function of the sensor, and that may be used in extremes of temperature and pressure in excess of 2000 bar and temperatures up to 200° C. and higher, making them useful for process applications including downhole measurement of drilling, cementing, and formation fluids in oil, gas and geothermal exploration, completion, and production.

The method of using a vibrating elastic wire for measuring the properties of a fluid, including density and viscosity, is well known. [Vibrating Wire Viscometer; J. T. Tough, W. D. McCormick, and J. G. Dash; Rev. Sci. Instrum. 35, 1345 (1964); U.S. Pat. Nos. 8,166,812 and 7,194,902, among others]. In a typical embodiment of such a method, a conductive wire is stretched between two supports, which are electrically insulated from one another. The wire is immersed in a transverse magnetic field. A current passed through this wire results in a Lorentz force being applied to the wire, in a direction mutually perpendicular to the magnetic field, on the one hand, and to the direction of the current (in this case, the longitudinal axis of the wire) on the other.

Such a wire has a resonant frequency in air that is dependent on its density, axial tension, and to a degree dependent on the ratio of its diameter to its length, also on its elastic moduli. If an oscillating current is passed through the wire at a frequency near its resonant frequency, the wire will oscillate in a direction perpendicular to the transverse magnetic field, and will continue to oscillate even after the current is shut off. Alternatively, the wire may be excited with a step function of direct current, and will oscillate at its resonant frequency when the current is shut off.

This continuing transverse oscillation will result in a current being induced in the wire, because it is a conductor moving in a magnetic field. This induced current can be used to monitor the decay of the wire's oscillations. The decay time of the oscillations is a measure of the wire's mechanical damping, which is itself dependent on the characteristics of the wire, and more particularly, the characteristics of a fluid in which it may be immersed. The decay time of the oscillations is dependent on both the density and the viscosity of the fluid, or more specifically, on the product of density and viscosity.

In fact, any of several methods may be used to measure the damping of the wire, including but not restricted to:

1. The wire may be excited with a periodic current, and its deflection measured by other means, as for example, an optical transducer.
2. The electrical impedance of the wire may be measured over a range of frequencies near its resonant frequency, and from the complex impedance curves, together with a theoretically or empirically derived model, the viscosity and density of the fluid may be inferred.
3. The resonance of the wire may be excited by an electrical transient, and the resulting oscillation measured by the current induced in the oscillating wire.
4. The resonant wire may be made part of a gated phase-locked loop, of the kind described in U.S. Pat. No. 5,837,885 and in U.S. Pat. No. 8,291,750.

Any of these methods may be used singly or in combination with one another, the ultimate goal being to measure the damping and resonant frequency of the wire. In general, both the damping and the resonant frequency of the wire will be influenced by both the density and the viscosity of the fluid. By use of suitable empirical and/or theoretical models, the influences of density and viscosity may be separately determined, and these two properties derived from the measured damping and resonant frequency of the vibrating conductor.

This system has several disadvantages:

1. Its use is largely restricted to non-conductive fluids. Conductive fluids, such as salt solutions, will provide an alternative current path, perhaps even "short circuiting" both the driving current as well as the induced signal current.
2. In order to accurately measure the density of the fluid, the change in resonant frequency due to the fluid must be measured accurately. However, the "base" frequency—the frequency of the wire not loaded by fluid mass—must be known. This frequency is dependent on the tension of the wire. The two ends of the wire must be electrically insulated from one another. That means that the "mechanical circuit" comprising the wire and its support, will consist of materials with differing characteristics. This makes it complicated to predict the change of tension of the wire as a function of temperature.
3. The resonant frequency of the wire is determined by its density, length and axial tension. Generally, wires used for such devices must be very thin, making them vulnerable to mechanical damage, as by particles that may be present in the fluids whose characteristics are to be measured.

Some known techniques for attempting to address these problems include:

Providing an insulating coating for the wire, so as to avoid current flowing through the fluid. Such a coating may increase the damping of the wire, as well as the change in damping with temperature. Also, insulating coatings are seldom free of pores, and have a tendency to peel off with time, changing the mass of the wire and increasing its vulnerability to electrical conductivity and corrosive action of the fluid.

Making the insulating member of a material whose thermal coefficient of expansion matches that of the wire, making it simpler to predict the effect of temperature on the wire's resonant frequency. Such matching of expansion coefficients severely restricts the range of available materials, as well as typically being accurate over only a limited range of temperatures.

Another variant of this basic system relies on the elasticity of the conductor, rather than its axial tension. This can be achieved by forming the conductor into a loop whose ends are anchored in an insulating material. The loop acts mechanically as a beam-like structure, whose resonant modes are dependent on its elastic properties and its density. Such a system has been described in U.S. Pat. No. 8,291,750.

This improvement removes the restriction of making the resonant frequency dependent on the wire's tension, but leaves the problem of a bare or insulated wire being vulnerable to the fluid in which it is immersed. Also, the resonant frequency is still dependent on the mass and elasticity of the conductor, restricting the characteristics of the system to those dictated by the properties of the conductor.

A further restriction on the use of this device is that the electrical connections to the wire loop are themselves immersed in the fluid. In addition to the above-mentioned problems that may be created by insulating the wire and its connections, these connections become especially problematical when the device is to be used in high-pressure applications, such as in downhole fluid measurements in deephole drilling, such as in oil, gas, and geothermal exploration and production. In such applications, the electronics package that drives and monitors the sensor must be maintained at near-atmospheric pressure in a dry environment, which necessitates passing the leads of the sensor through a pressure barrier. Such feed-through devices must make a hermetic seal between the conductor, the insulator and the pressure barrier. Such seals are typically composed of polymeric resins that have temperature-dependent elastic properties and that therefore produce undesired temperature-dependent effects on the damping and resonant frequency of the loop.

SUMMARY

The present application discloses a general method of constructing a resonant fluid properties sensor in which a vibrating capillary tube is used as the resonator. An electrical conductor within the lumen of the capillary tube is used as a force and motion transducer, in which the excitation force is the Lorentz force generated by a current flowing in the conductor in a transverse magnetic field.

In a first separate aspect, a resonant fluid properties sensor includes an elastic tube defining an interior surface and a conductor threaded through the elastic tube. Solid material fills space between the conductor and the elastic tube interior surface, such that force generated by the conductor is directly transmitted to the elastic tube.

In a second separate aspect, a resonant fluid properties sensor has a solid structure defining a first aperture, and a second aperture. An elastic tube extent extends from the first aperture to the second aperture, and is attached to the sold structure about the first and second apertures, in a fluid impermeable manner. Finally, a conductor is threaded through the tubular element.

In a third separate aspect, a resonator has a solid structure defining a first aperture, a second aperture, a third aperture and a fourth aperture. A first elastic tube extent extends from the first aperture to the second aperture, and is attached to the sold structure about the first and second apertures, in a fluid impermeable manner. Also, a second elastic tube extent extends from the third aperture to the fourth aperture and is attached to the solid structure about the third aperture third and fourth apertures, in a fluid impermeable manner. Finally, a conductor is threaded through the tubular elements. This arrangement produces a motion of the resonant elements that is symmetric about a plane midway between the planes containing the resonant elements such that the reaction forces on the structures in which the resonant elements are mounted balance one another. This results in a balanced resonator analogous to a tuning fork, which minimizes leakage of energy into the surrounding structures, making the damping of the resonant structure largely independent of the means used to mount the sensor in a measurement system.

In a fourth separate aspect, a fluid properties measurement device includes a base and a torsional, longitudinal, or bending resonator, supported by the base and driven by means incorporated in the base. Also, a second resonator having at least a component of translational motion is supported by the base, and driven by means incorporated in the base.

DETAILED DESCRIPTION OF THE PREFERRED EMBODIMENTS

Generalized Resonator Structure

Figure 1:
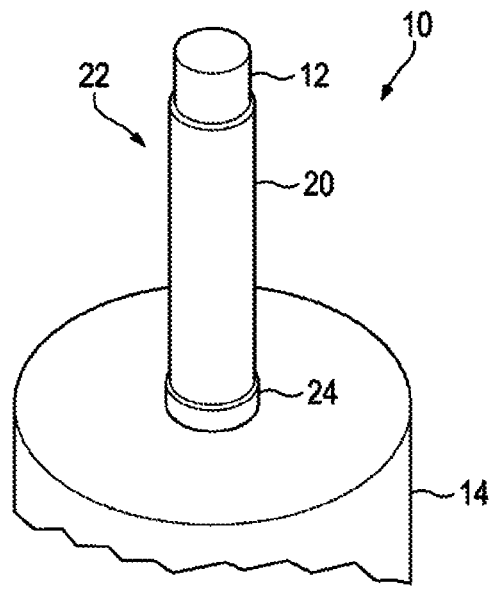
FIG. 1 is a top-side perspective view of a generalized structure for a resonant fluid properties sensor.

Referring to FIG. 1, in a first preferred embodiment a generalized structure for a resonator 10 (henceforth "structure 10") includes a conductor 12 that extends through elastic tube 14. Conductor 12 is used for exciting and sensing the motion of the elastic tube 14, and is completely electrically isolated from the elastic tube 14. As will be seen, this allows making structure 10 into a single hermetically sealed unit so that there is no possibility of any portion of conductor 12 contacting the fluid (not shown) into which structure 10 will be placed. This eliminates all problems stemming from the need to electrically insulate the conductor 12 from this fluid. It also eliminates the need for insulating coatings that have been used in the prior art to insulate and protect a conductor similar to conductor 12 from the fluid in which the conductor is directly immersed. These coatings have been vulnerable to abrasion, corrosion, and porosity that would expose the underlying conductor to the surrounding fluid.

As noted, structure 10 is constructed in part of the elastic tube 14, which is typically composed of a material with high elastic modulus, such as metal, ceramic or glass. The elastic tube 14 defines a lumen that is much narrower than the outer diameter of elastic tube 14. Conductor 12, is provided covered with insulation 20, as part of an insulated wire 22, which is passed through the lumen of elastic tube 14. The insulated conductor 12 is then joined to elastic tube 14 in such a way as to ensure that any force produced by the conductor 12 is transmitted to the elastic tube 14, and that any motion of the elastic tube is transmitted to the conductor. One method for accomplishing this includes filling any voids between the conductor and the interior surface of elastic tube 14 with a semi-rigid sealant 24, which is preferably an epoxy resin or ceramic potting material. Said insulation 20 differs from said insulation of prior art in that it serves only to prevent said conductor 12 from electrically contacting elastic tube 14 during the step of filling voids between the conductor and the tube with sealant 24. It is not exposed to the fluid, and therefore is not prone to the limitations of insulating coatings in prior art.

Figure 2:
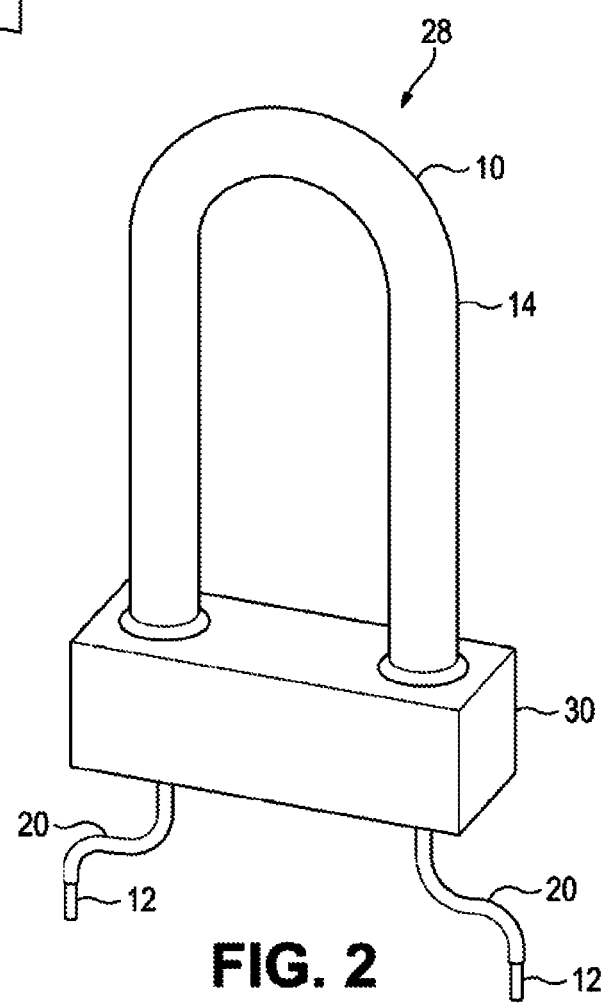
FIG. 2 is a top-side perspective view of a resonant fluid properties sensor, constructed using the generalized structure of FIG. 1.

Referring to FIG. 2 below, a resonator 28 is produced by first bending the elastic tube 14 into the shape of a "U", and welding, brazing or soldering the legs of the U into holes in a metal plate 30, ensuring a hermetic seal between the plate and the outer surface of the elastic tube 14. Although resonator 28 is shown as having a U-shaped structure, it could be shaped otherwise.

Conductor 12 is passed through the lumen of elastic tube 14, which is then filled with a fluid resin, which may be an epoxy having a rigid hardened state, which is then hardened into hardened sealant 24. A force- and motion-transmitting bond is thereby created between the conductor 12 and the elastic tube 14. The ends of the conductor 12 emerge from the lower side of the plate 30 which is part of a structure separating the fluid from the electrical connections, thus protecting ends from the fluid into which the elastic tube 14 and plate 30 may be immersed.

In a preferred embodiment elastic tube 14 takes the form of a stainless steel tube having a 1.6 mm outer diameter and an inner diameter of 0.13 mm, or less than 1/10 of its outer diameter. Conductor 12, takes the form of an insulated copper wire having a 0.011 mm outer diameter that is passed through the lumen of elastic tube 14, and the space between the conductor 12 and the interior surfaces of elastic tube 14 is filled with an unpolymerized epoxy resin with the help of a vacuum drawn on one end of the capillary. Because the resultant epoxy coating 24 is so thin, even a rigid epoxy resin will be sufficiently flexible to allow subsequent bending of conductor 12 and elastic tube 14 into the shapes required for specific sensor applications.

Insulated wire 22 may consist of the conductor 12, in the form of a copper core wire of the type referred to in the industry as "magnet wire", covered by insulation 20, which takes the form of a thin conformal polymeric insulation layer, for example a high-temperature polyimide coating.

Structure 10 may be formed into various resonator shapes useful for measurement of fluid properties. In the following descriptions, the internal structure is omitted, with only the generalized structure 10 or outer elastic member 14, and where relevant the direction of current flow through conductor 12, indicated.

Modes of Operation

There are various modes of operation for resonator 28, and other resonators of differing shapes formed from generalized structure 10. specialized for various fluid properties measurements tasks.

The basic mode of operation is to produce a force, either impulsive or periodic, in the resonator 28 by passing a current from a source of current through its conductor 12. To sense the motion of the resonator 28, its conductor 12 is connected to a current sensing device that senses the current induced in the conductor 12 by its motion in the magnetic field. Alternatively, a voltage sensing device may be connected to the conductor 12 to sense the voltage produced across the terminals of the conductor by the conductor's motion in the magnetic field.

The resonator's conductor may be connected to a gated phase-locked loop circuit, such as is disclosed in patents U.S. Pat. Nos. 5,837,885 and 8,291,750. In this mode, the resonator is alternately excited and sensed, with the phase locked loop circuit producing the proper frequency to maintain a prescribed phase difference between the driving frequency and the resonator's motion. This allows measurement of both damping and resonant frequency of the resonator.

In a balanced form of the resonator, in which two elastic elements are mounted on a common base, as in FIGS. 6-10 below, one elastic element may be used as an exciting transducer, and the second as a sensing transducer, provided that the mechanical coupling between the two elements is sufficiently strong. This coupling may be enhanced with a stratagem illustrated in FIG. 9 below, in which a compliant element is disposed between the mounting plate carrying the two elastic elements, and the base of the sensor. This compliant element both enhances the coupling of the two resonators, and reduces energy leakage from the resonators into the surrounding structures, thereby decreasing the sensor's intrinsic damping and increasing its sensitivity to low-viscosity fluids.

Another mode of operation may be facilitated by replacing the central conductor 12 in tube 14 with two parallel conductors (not shown) that are electrically isolated from one another. A first one of these conductors can serve to carry the driving current, and a second one of the conductors can be used to sense the motion of the resonator.

The resonators may be excited by an impulsive waveform, such as a DC step function, or a square pulse, through the central conductor, and the decay of the resultant resonance measured using the current induced in the central conductor by the motion of the resonator in the external magnetic field.

Other modes are conceivable, using, for instance heterodyne mixing processes to achieve high sensitivity and electrical noise suppression. It is possible, for instance to superimpose an oscillating magnetic field component on the constant bias field supplied by the electro- and/or permanent magnet. Since the Lorentz force on the resonator is proportional to the product of the current through the conductor and the external magnetic field, the force produced by an oscillating current and an oscillating magnetic field will contain components at both the sum and the difference of the frequencies of the current and the field. If the two frequencies are adjusted such that their sum or differences is equal to the resonant frequency of the resonator, the resonator will be driven at its resonant frequency. If the magnetic bias field has a constant or DC component, it will induce a current in the resonator's conductor that is at exactly the resonant frequency. A suitable system of filters can synchronously detect the induced current at precisely the resonant frequency, while suppressing the driving current's frequency. In this way, a CW, or continuously driven resonator may be made that is not dependent on the gated phase locked loop or other transient measurement procedures.

Resonator Configurations

U-shaped resonator 28 can be excited in at least three vibrational modes, each of which has a fundamental as well as higher order modes.

Figure 3A:
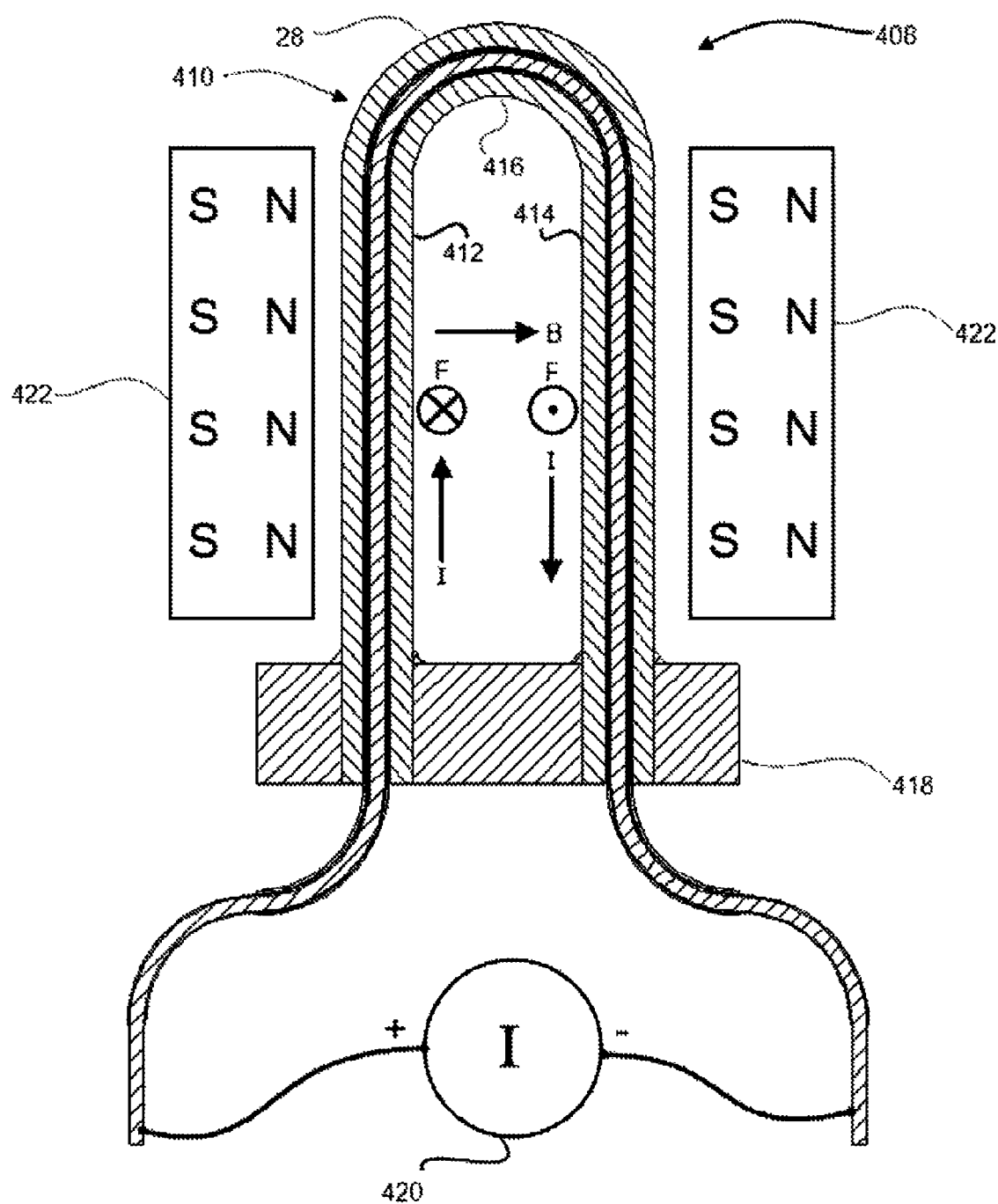
FIG. 3A is an illustration of an additional alternative preferred embodiment of a sensor configuration.

Referring to FIG. 3A, resonator assembly 28 forms a portion of sensor assembly 408, which includes an elastic capillary loop 410. A measurement of the damping of induced vibrations in this loop 410, as performed by driving and measurement system, can be used to determine the properties of a fluid in which the loop has been introduced. These properties are not limited to fluid viscosity, but include density and elasticity. In addition, a system, equipped with sensor 408 can be used to measure the damping and elasticity of gels and other mechanically compliant solids.

Figure 3D:
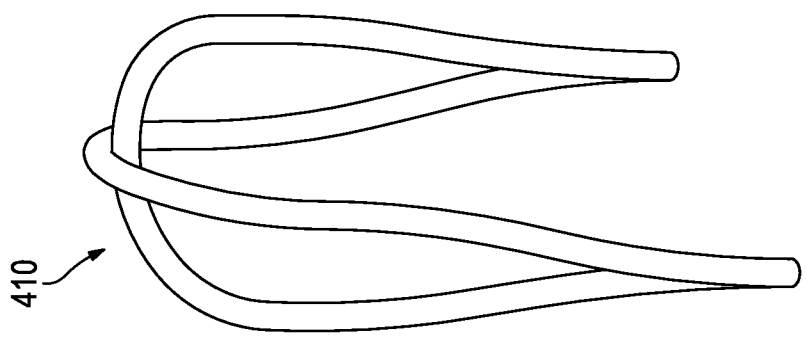
FIG. 3D is still another additional illustration of the sensor configuration of FIG. 3A, showing maximum torsion of the capillary loop.
Figure 3C:
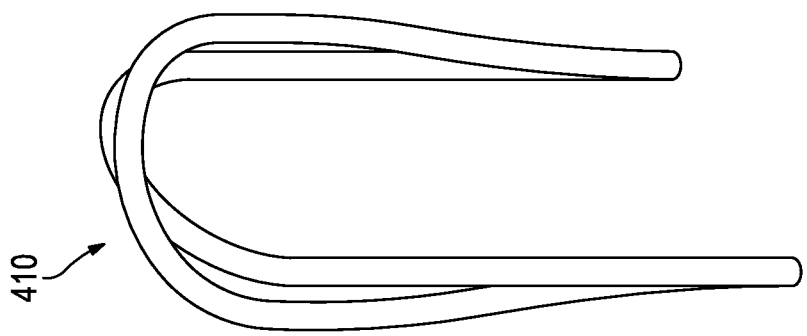
FIG. 3C is another additional illustration of the sensor configuration of FIG. 3A, showing torsion of the capillary loop.
Figure 3B:
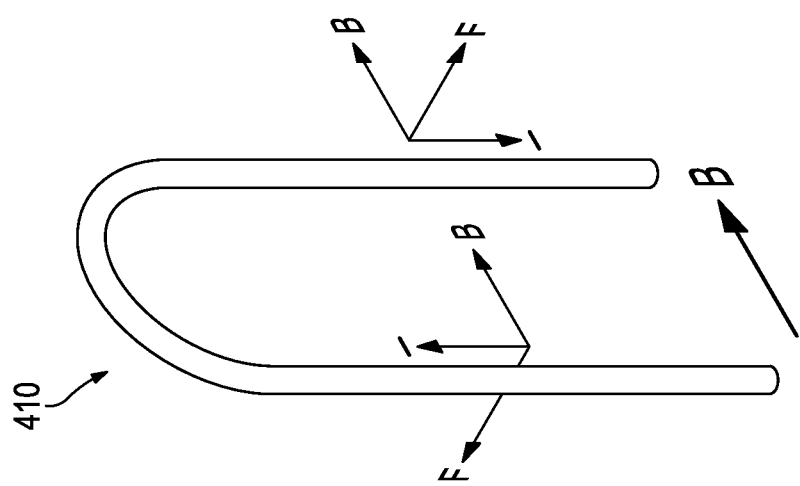
FIG. 3B is an additional illustration of the sensor configuration of FIG. 3A, showing the direction of magnetic flux.

The loop 410, which is formed of structure 10, includes a first leg 412, a second leg 414 and a bridge 416 joining the two. Also, a massive, base 418 supports loop 410. Loop 410 is shown welded into base 418, although it could also be attached by brazing, soldering or with an adhesive. A current source 420, drives a current through the loop 410. Additionally, a pair of magnets 422 create a magnetic field B that is traversed by loop 410. Accordingly as current I is passed through loop 410, it is acted upon by a mechanical force F proportional at each point to the vector product of the magnetic field and the current through that segment, causing a mechanical distortion of loop 410. As the current direction in legs 412 and 414 is mutually opposed, this creates opposite forces in legs 412 and 414, acting to twist loop 410, as shown in FIGS. 3B, 3C and 3D. Furthermore, because the material of the loop 410 possesses both inertia due to its mass, and elasticity, when the loop 410 is distorted and released, it will vibrate at one of its characteristic frequencies, thereby having a set of vibratory modes. If the current source produces an alternating current, its frequency may be adjusted such as to preferentially excite one of the resonant modes of the capillary loop.

Figure 4A:
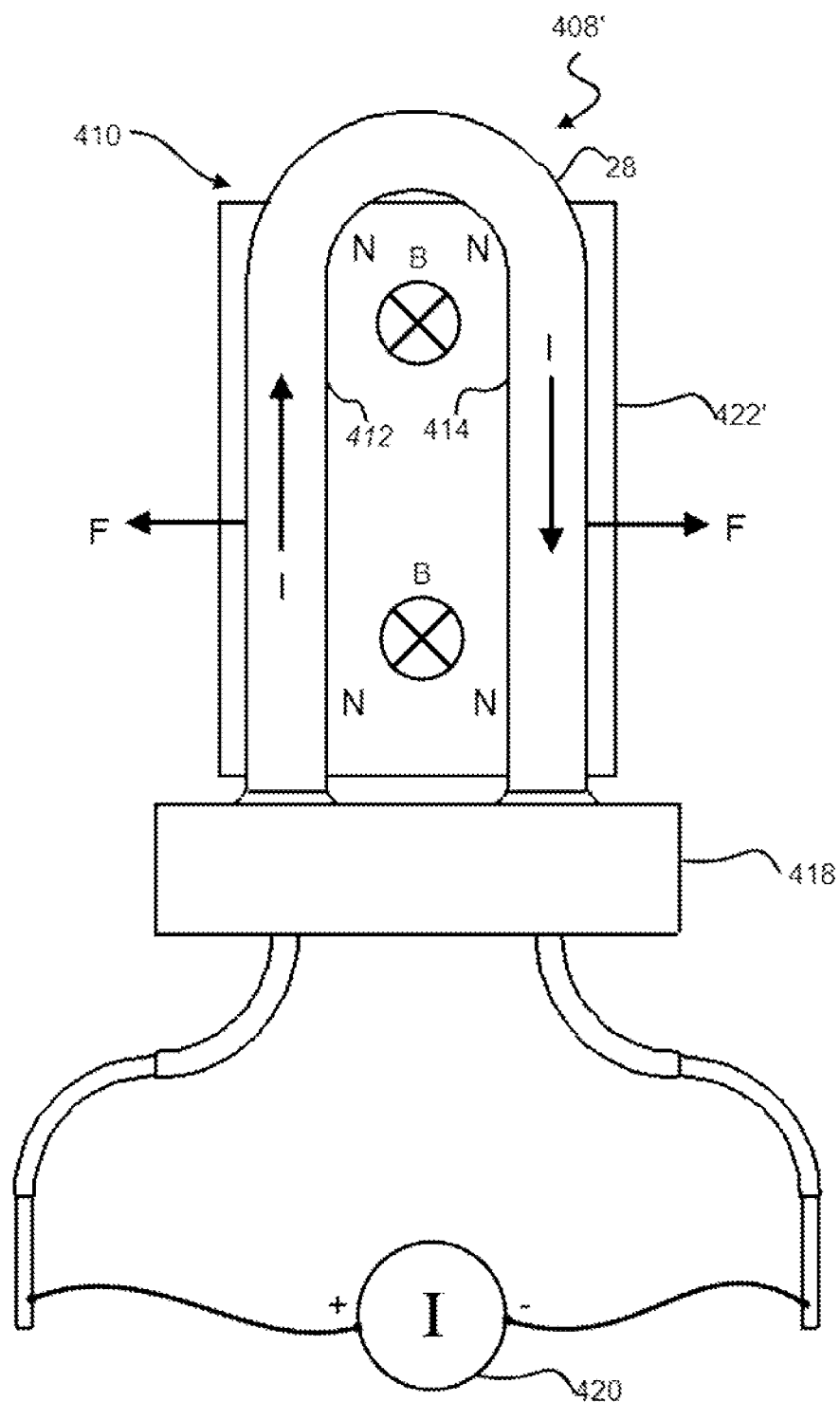
FIG. 4A is an illustration of another additional alternative preferred embodiment of a sensor configuration.
Figure 4D:
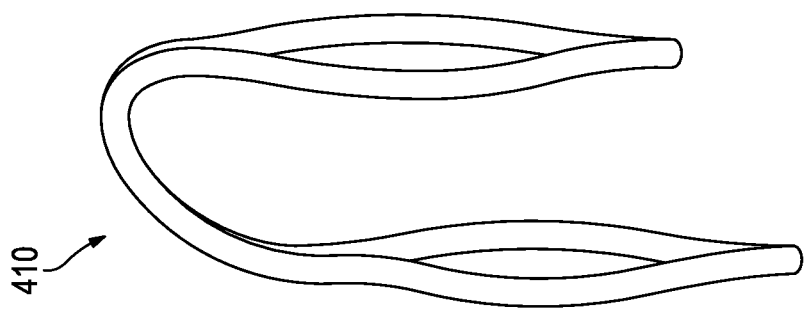
FIG. 4D is still another additional illustration of the sensor configuration of FIG. 4A, showing maximum planar distension of the capillary loop.
Figure 4C:
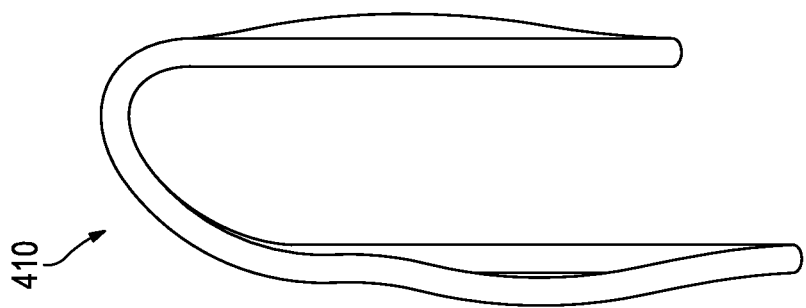
FIG. 4C is another additional illustration of the sensor configuration of FIG. 4A, showing planar distension of the capillary loop.
Figure 4B:
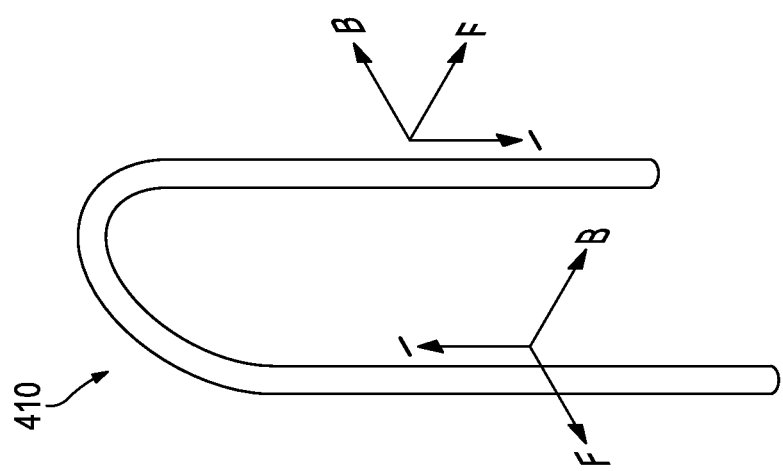
FIG. 4B is an additional illustration of the sensor configuration of FIG. 4A, showing the direction of magnetic flux.

Referring to FIG. 4A, a sensor configuration 408' includes magnets 422' that are positioned behind and in front (not shown) of the loop 410, with opposing poles facing each other. The resulting magnetic field B is perpendicular to the plane of the loop 410, so that the force F on the legs 412 and 414, through which current I passes on conductor 12, of the loop is in the plane of the loop 410, and either inward toward its symmetry axis, or outward away from its symmetry axis depending on the polarity of the current source 420. The legs of the loop function like the tines of a tuning fork in which the tips of the tines are connected by an elastic member. This is shown in FIGS. 4B, 4C and 4D. FIG. 4B illustrates the magnetic, current and force vectors operating on the loop 410. FIG. 4C shows the static distortion of the loop 410 compared to its initial undistorted shape. FIG. 4D shows the limits of the motion of the loop 410 when it is driven by magnets 422' as shown in FIG. 4A.

Figure 5A:
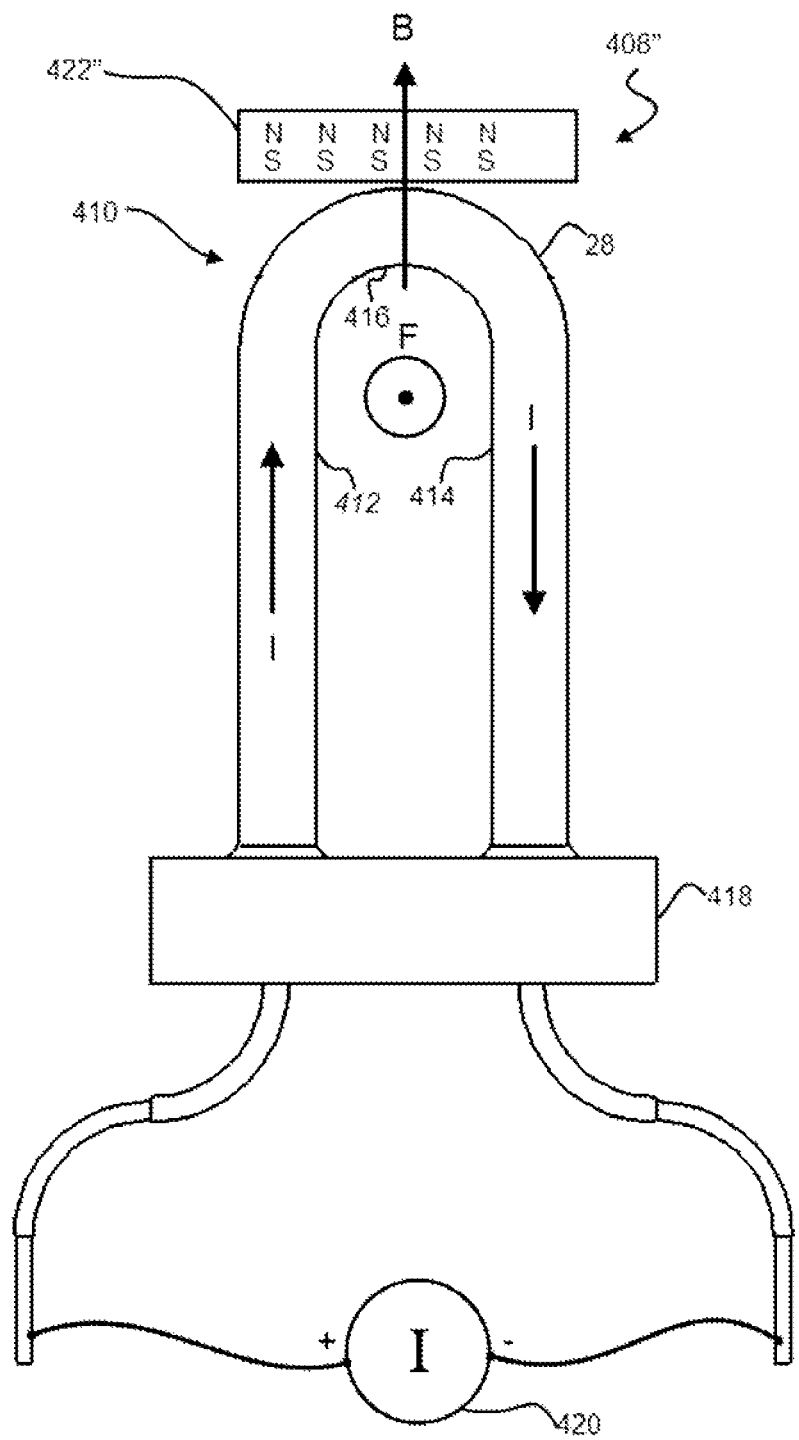
FIG. 5A is an illustration of another additional alternative preferred embodiment of a sensor configuration.
Figure 5D:
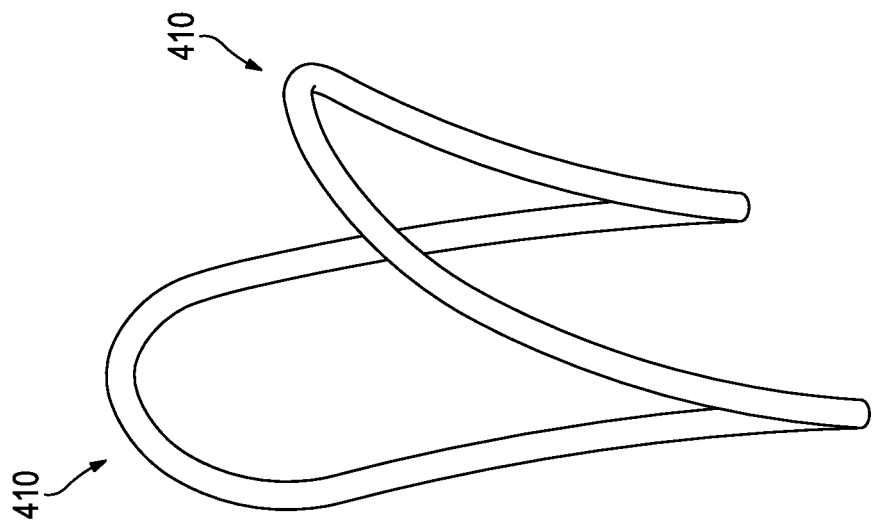
FIG. 5D is still another additional illustration of the sensor configuration of FIG. 5A, showing maximum bending of the plane of the capillary loop.
Figure 5C:
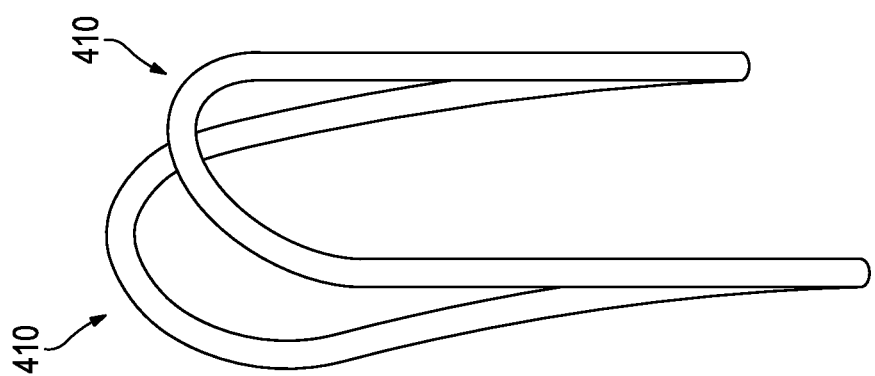
FIG. 5C is another additional illustration of the sensor configuration of FIG. 5A, showing bending of the plane of the capillary loop.
Figure 5B:
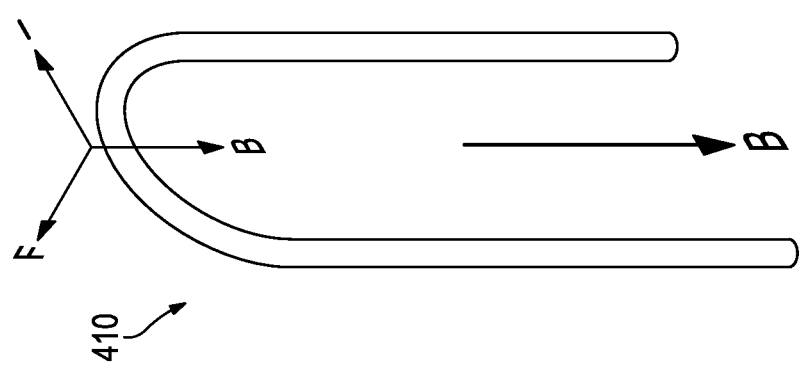
FIG. 5B is an additional illustration of the sensor configuration of FIG. 5A, showing the direction of magnetic flux.

Referring to FIG. 5A, a sensor configuration 408" includes a magnet 422" that is positioned above the arch 416 of the loop 410. Referring to FIG. 5B, the magnetic field of magnet 422 is parallel to the plane of the loop and parallel to the current flow in its legs 412 and 414, with only bridge 416, which is not parallel to the field, experiencing a force, resulting in bridge 416 being pushed into and out of the paper, as shown in FIG. 5C and with FIG. 5D showing the limits of the motion of the loop when driven in the sensor configuration 408".

When the loop is immersed in a fluid or compliant solid, each of the sensor configurations 408, 408' and 408" produces a somewhat different pattern of flow or distortion in the medium. The vibrational characteristics created by the differing sensor configurations 408, 408' and 408" will be influenced to differing degrees by the characteristics of the medium. Therefore, the sensor configuration, and therefore the vibratory frequencies, can be selected to separate the effects of various properties of the medium.

Moreover, in additional preferred embodiments the magnets are not oriented the along a principal axis of the loop, as is shown in FIGS. 3A, 4A and 5A. In one preferred embodiment of a sensor configuration, the magnetic field is oriented at a nonzero angle to each of the principle axes, permitting all of the mode geometries cited above to be generated by a single sensor configuration.

Many variant embodiments also exist for the arrangement of the magnets. For example, although two magnets are shown in the embodiments of FIGS. 3A and 4A, a single magnet could suffice to create the required magnetic field, for the capillary geometries shown. Alternatively, a magnetic loop could be used to create the required magnetic field.

Balanced U Resonators

The configurations of FIGS. 3A-3D and 4A-4D are unbalanced, in the sense of producing appreciable reaction forces on the base in which they are mounted. The configuration of FIGS. 3A-3D produces a net torque around an axis connecting the two legs of the U and parallel to the plane of the base. The configuration of FIGS. 4A-4D produces a net torque about an axis in the plane of the resonator, parallel to the legs, and passing through the midpoint of the bridge. Only the configuration of FIGS. 5A-5D is intrinsically balanced, since the bending forces transmitted to the base by the two legs are equal and opposite, and in the same plane.

Figure 6:
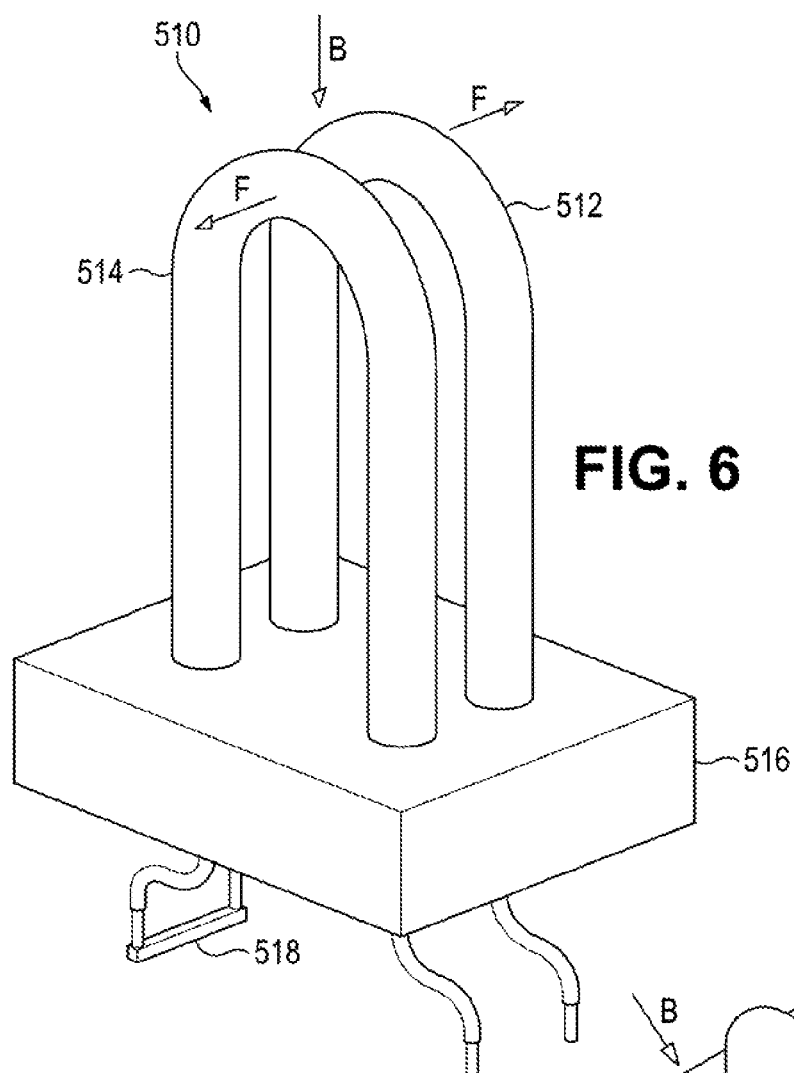
FIG. 6 is a top-side perspective view of an alternative embodiment of a resonant fluid properties sensor, according to the present invention, shown in a magnetic field of a known direction, showing the force vectors thereby created.

Referring to FIG. 6, a balanced resonator 510 includes a first U-shaped resonant element 512 and a second U-shaped resonant element 514 mounted into plate 516, with their planes parallel to one another, and their mid-planes coincident. The applied magnetic field B is again in the plane of the resonators and parallel to their legs. The direction of the current in U-shaped resonant element 514 is opposite to the direction of current in U resonator 512. This is accomplished by connecting their conductors in series by conductive bridge 518. Accordingly, the two U-shaped resonant elements 512 and 514 experience opposing forces F from the applied magnetic field and vibrate in antiphase to one another. The F arrows shown in FIG. 6 could both be reversed, but they always point in opposite directions. This configuration or mode may be referred to as "flapping mode."

Figure 7:
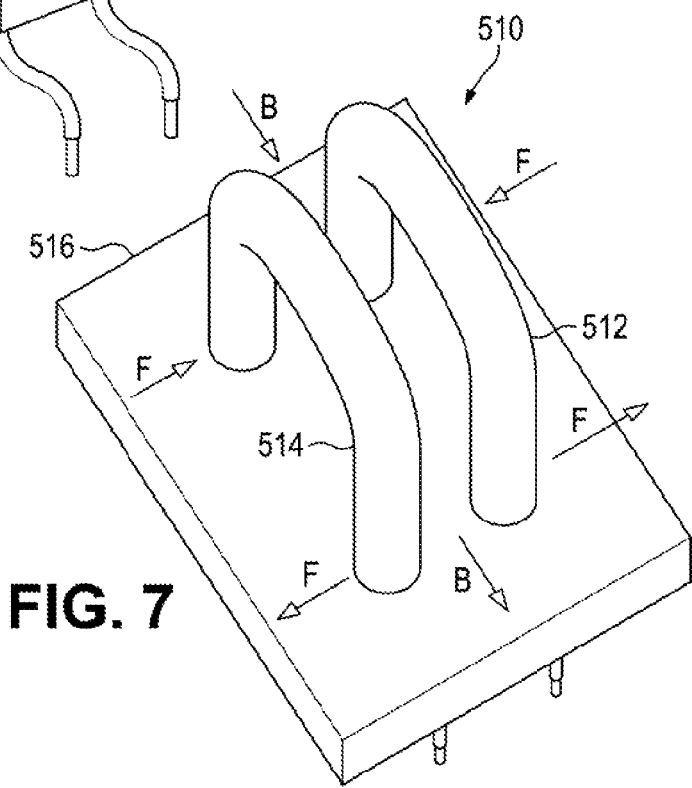
FIG. 7 is a top-side perspective view of the resonant fluid properties sensor of FIG. 6, shown at a rotated angle and exposed to a magnetic field having a different direction from that of FIG. 6, and showing the force vectors thereby created.

Referring to FIG. 7, in another configuration, resonator 510 is placed in a magnetic field that is parallel to the planes of the "U," but perpendicular to the legs of the individual U-shaped resonant elements 512 and 514. As noted above, resonant elements 512 and 514 are connected in series so as to have equal but opposite current flows, as before producing forces F, that are in opposite directions, but which are different from the configuration of FIG. 6, in that both resonant elements 512 and 514 are placed into torsion, as shown. These forces are, as in the configuration of FIG. 6, are balanced as they apply to the mounting plate 516. A problem is sometimes encountered, however, in resonator 510 and similarly constructed resonators, in that small differences in physical characteristics of elements 512 and 514, caused by imperfect repeatability in the manufacturing process, can result in a decoupling of the vibratory movement under various conditions.

Figure 8:
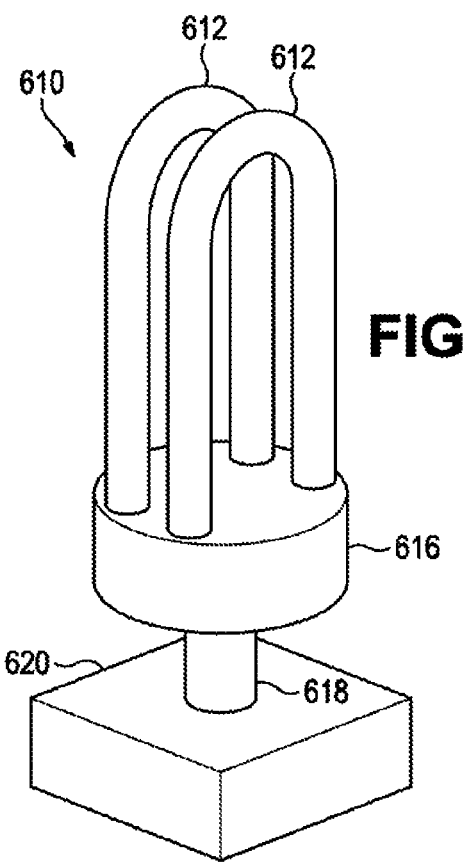
FIG. 8 is a top-side perspective view of another alternative embodiment of a resonant fluid properties sensor according to the present invention.

Referring to FIG. 8, a dual-U resonator 610 includes U-shaped resonant elements 612 mounted on a mechanical-coupling base 616, which is supported by a compliant column 618. A massive base 620 supports column 618. Resonator 610 can tolerate a greater degree of asymmetry between resonant elements 612, without suffering a decoupling of resonant motion, than resonator 510 can tolerate between elements 512 and 514.

In the above embodiments, the magnetic field that interacts with the current-carrying conductors may be created by either permanent or electromagnets, or some combination of the two. The advantage of using an electromagnet is that it may be periodically de-energized so that any magnetic particles that have been attracted to the sensor may be washed away by the process stream in which the sensor is immersed. All of the above embodiments require extra structures on which to mount the bias magnets.

Figure 9:
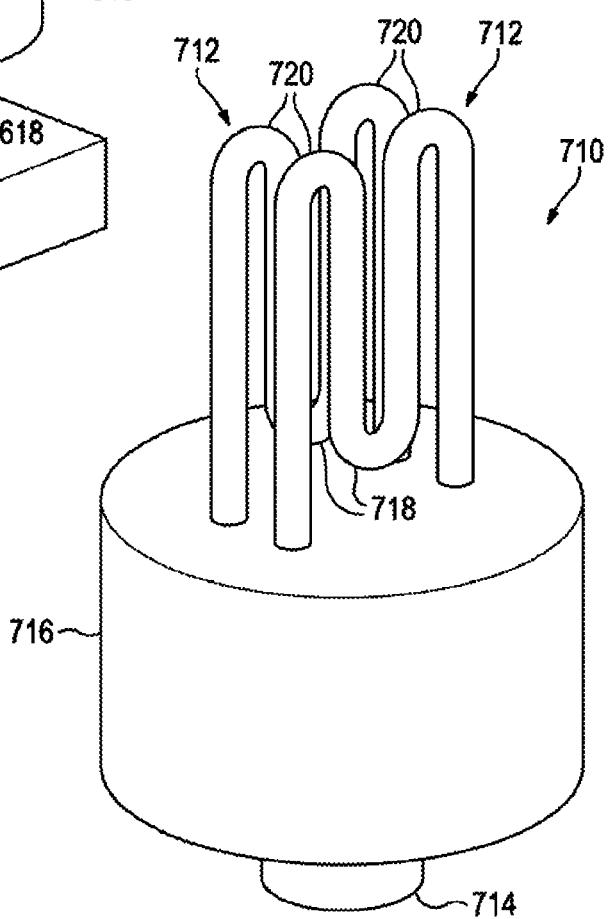
FIG. 9 is a top-side perspective view of still another alternative embodiment of a resonant fluid properties sensor, according to the present invention.
Figure 10:
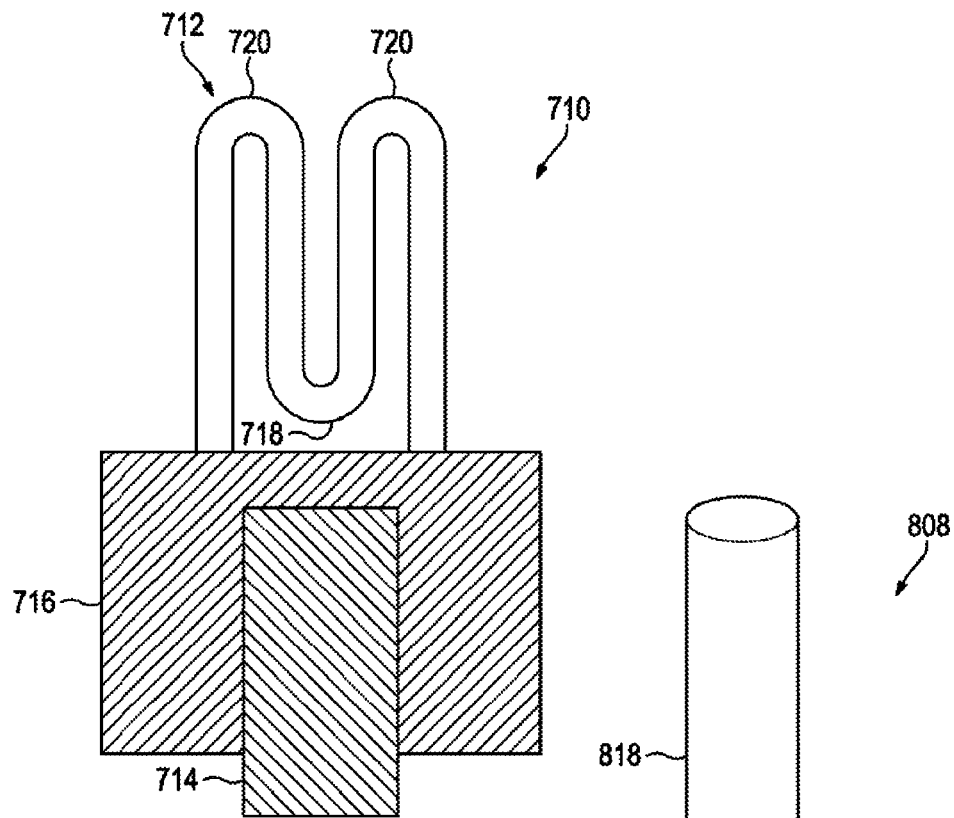
FIG. 10 is a sectional view of the resonant fluid properties sensor of FIG. 9.
Figure 11:
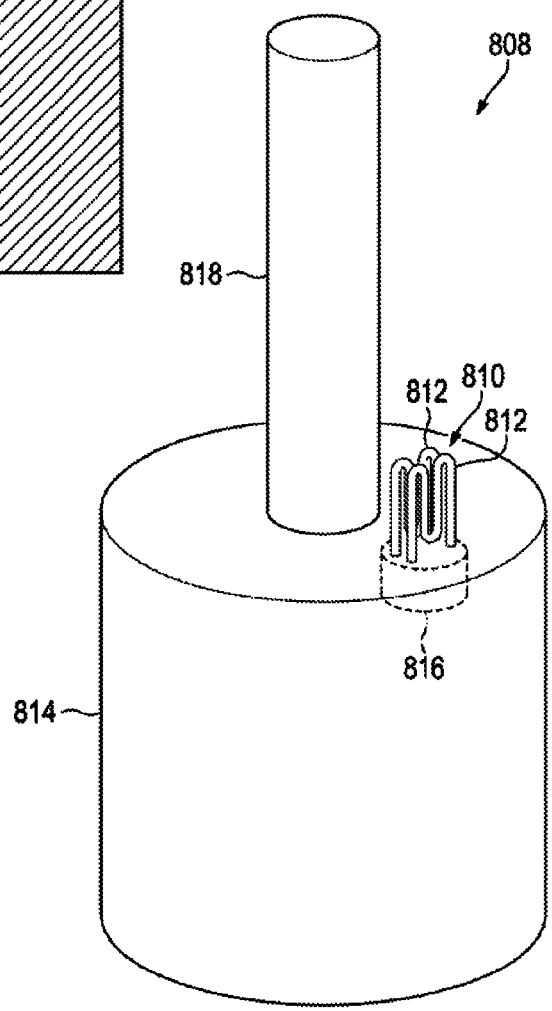
FIG. 11 is a top-side perspective view of a fluid measurement apparatus having both a torsional resonator and a translational motion resonator.

Referring to FIGS. 9 and 10, a particularly advantageous resonator embodiment 710 includes two M-shaped (with rounded points) resonant elements 712, which allows a bias magnet 714 to be embedded in a base 716 of the resonator 710. This configuration obviates extra structures to contain a bias magnet, and resulting in simpler mounting and construction. Resonant elements 712 are anchored by their outer legs in such a way as to leave some minimal clearance between a central, lower bridge 718 of each M-shaped element 712, and the base 716. The bias magnet 714 is embedded in the base of the sensor such that its field is in the plane of elements 712, and perpendicular to its lower central bridge. This results in a force on both the central bridge 718, and the two upper bridges 720 of each element 712. However, the force is greatest on the lower central bridge, causing symmetric bending of elements 712. Similar to the case for embodiments disclosed above, the bias magnet 714 may be either an electromagnet or a permanent magnet. The greatest force on elements 712, caused by the magnetic field of magnet 714 is applied to each lower bridge 718. The flexibility provided by way of the long portions of each element 712 that connects each lower bridge 718 to the base 716, results in a greatly reduced incidence of harmful decoupling between elements 712. In an alternative embodiment (not shown) a single M-shaped resonant element is used.

Resonator 710 also displays a higher-order bending or flapping mode, in which each of the upper bridges 720 move in the opposite direction to its corresponding lower bridge 718. The decoupling of elements 712 from the base 716, during this mode, is even greater than for the first bending mode described above since the higher order modes are "self balancing" and exert a lower torque on the base.

Further, the same configuration of two M-shaped elements 712 may be driven in a torsional mode if the bias field is made parallel to the plane of the elements 712 and perpendicular to the legs of elements 712, although the electromagnetic coupling of this mode will be diminished because of the complex pattern of ascending and descending currents in each member.

Finally, the in-plane "breathing" mode may be excited in two parallel M shaped elements operating in antiphase. This configuration will give the greatest degree of decoupling from the base by balancing out almost all of the reaction forces generated by the system's vibrations.

Temperature Compensation and Measurement

Resonant elements 410, 512, 612, 712 and 812 all vibrate perpendicular to their own surfaces over at least a portion of that surface. This perpendicular motion imparts a velocity to the surrounding fluid, which increases the inertia of the resonator. The increase in inertia has the effect of lowering the resonant frequency of the resonator, nearly in proportion to the density of the fluid. The resonant frequency of the sensor is therefore a measure for the density of the fluid, while its damping is a measure of the density-viscosity product of the fluid.

Most materials, such as stainless steel, suitable for the construction of such resonators have elastic constants that depend on the temperature of the material. These elastic constants generally decrease with increasing temperature, resulting in lowering of the resonant frequency. If the resonant frequency of the sensor is to be used to measure the density of the fluid, it is necessary to compensate this frequency for the temperature at which the sensor is operating.

Elements having generalized structure 10, have features that allow them to be used to measure their own temperature. Each of these resonators is driven by a thin conductor 12 passing through its central channel. If the function describing the dependence of this wire's resistivity on temperature is known, the wire 12 can be used to measure the temperature of the sensor. This is accomplished by measuring the voltage across the wire as it is excited by a current having a known waveform. This measurement can be done during the excitation phase of the sensor's operating cycle, or alternatively, it can be done during pauses in that cycle. In the most advantageous embodiment, the wire 12 would be supplied with a low-level AC current of several milliamperes—sufficiently small to avoid significant self-heating of the wire 12—and a synchronous detector used to measure the voltage across the wire 12. If the voltage and current are known, the resistance of the wire 12 can be calculated and, together with the formulas governing the relationship of elastic moduli of tube 14 to temperature and resonance frequency to elastic moduli of tube 14, the thermal offset frequency of the resonance can be calculated and used to correct the density measurement.

Density Measurement Adjunct for Torsional-Resonator Viscometers

Viscometers that operate by measuring the damping of a torsional resonator are well known. In general, the damping of these resonators depends on the product of density and viscosity. In order to measure either the dynamic or kinematic viscosity of a fluid with this kind of viscometer, an independent measurement of density must be made. The capillary-loop resonators disclosed here may be used as an adjunct to a conventional torsional-vibrational viscometer to permit measurement of absolute viscosity, independent of the density.

In an additional preferred embodiment, a torsional viscometer 808, includes a resonator 810, that is very similar to resonator 710, including two M-shaped resonant elements 812, protruding from a base 814 of viscometer 810, and a magnet 816 embedded into base 814. Viscometer 810 uses a torsional element 818 to measure a first quantity most closely related to viscosity, and uses resonator 812 to measure a second quantity most closely related to fluid density. A data processor then uses both the first and second quantities to arrive at an enhanced measurement of both viscosity and fluid density.

The damping and resonant frequency of the resonator 810 is used to calculate the density of the fluid, and this calculated value is used to calculate the dynamic and/or kinematic viscosity of the fluid in which the assembly is immersed.

The generalized structure 10 permits making sensors that are impervious to extremes of temperature and pressure, making them useful for process applications including downhole measurement of drilling, cementing, and formation fluids in oil, gas and geothermal exploration, completion, and production. This method of producing fluid properties sensors has an advantage over prior art in that its operation does not rely on permanent magnets in close proximity to the sensor, which in the presence of fluids containing suspended magnetic particles, could otherwise interfere with the proper operation of the sensor.

Moreover, generalized structure 10 enables a nearly unlimited range of embodiments adaptable to measuring fluid properties over a wide range of viscosities and densities, in a wide variety of mechanical housings adaptable to a wide range of applications. Resonant elements 410, 512, 612, 712 and 812 are, in one preferred embodiment, all made of structure 10.

Frame and Linear Resonator Embodiment

Figure 12:
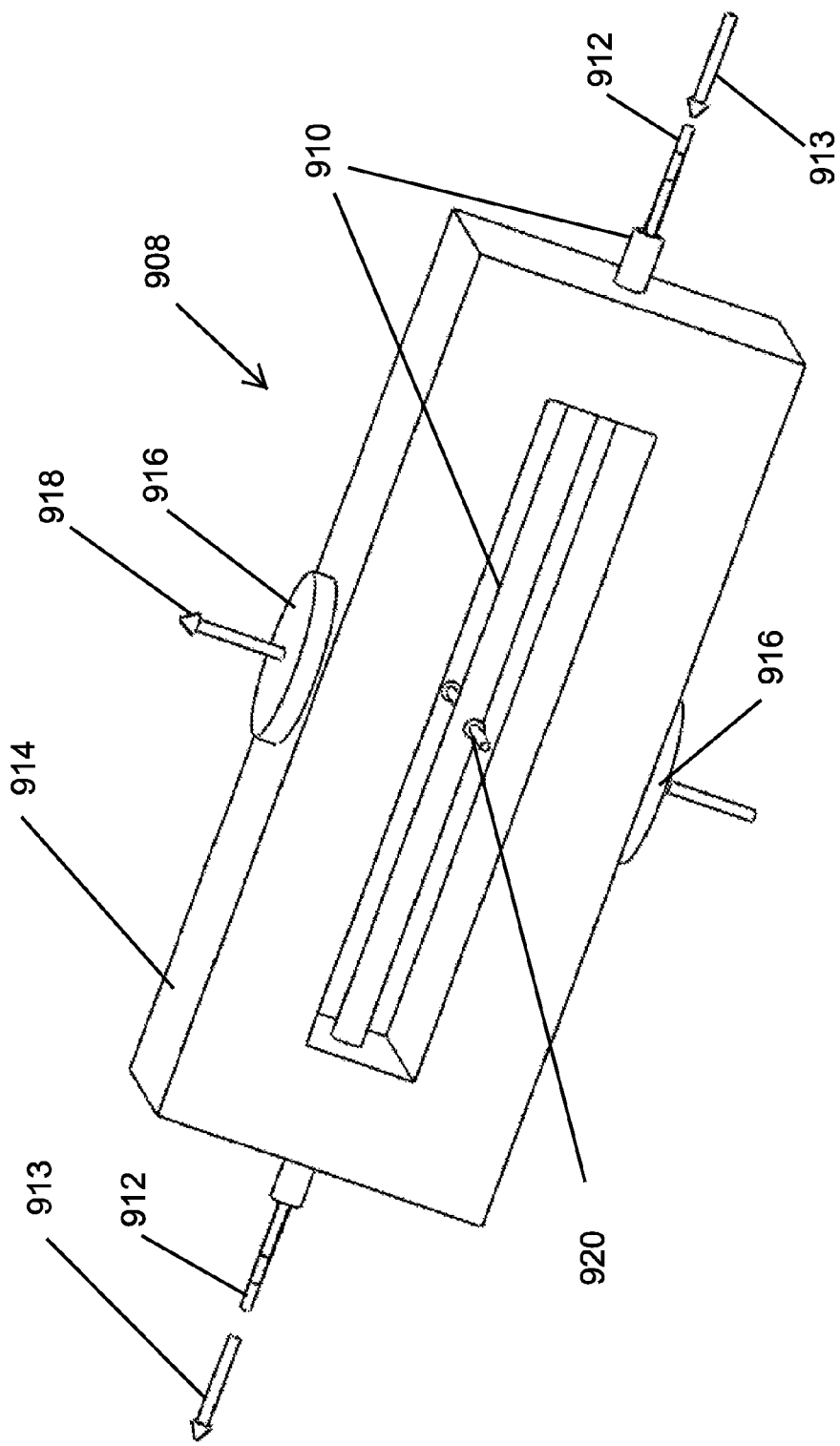
FIG. 12 shows one embodiment of a resonant fluid properties sensor constructed with a straight capillary resonator.
Figure 13:
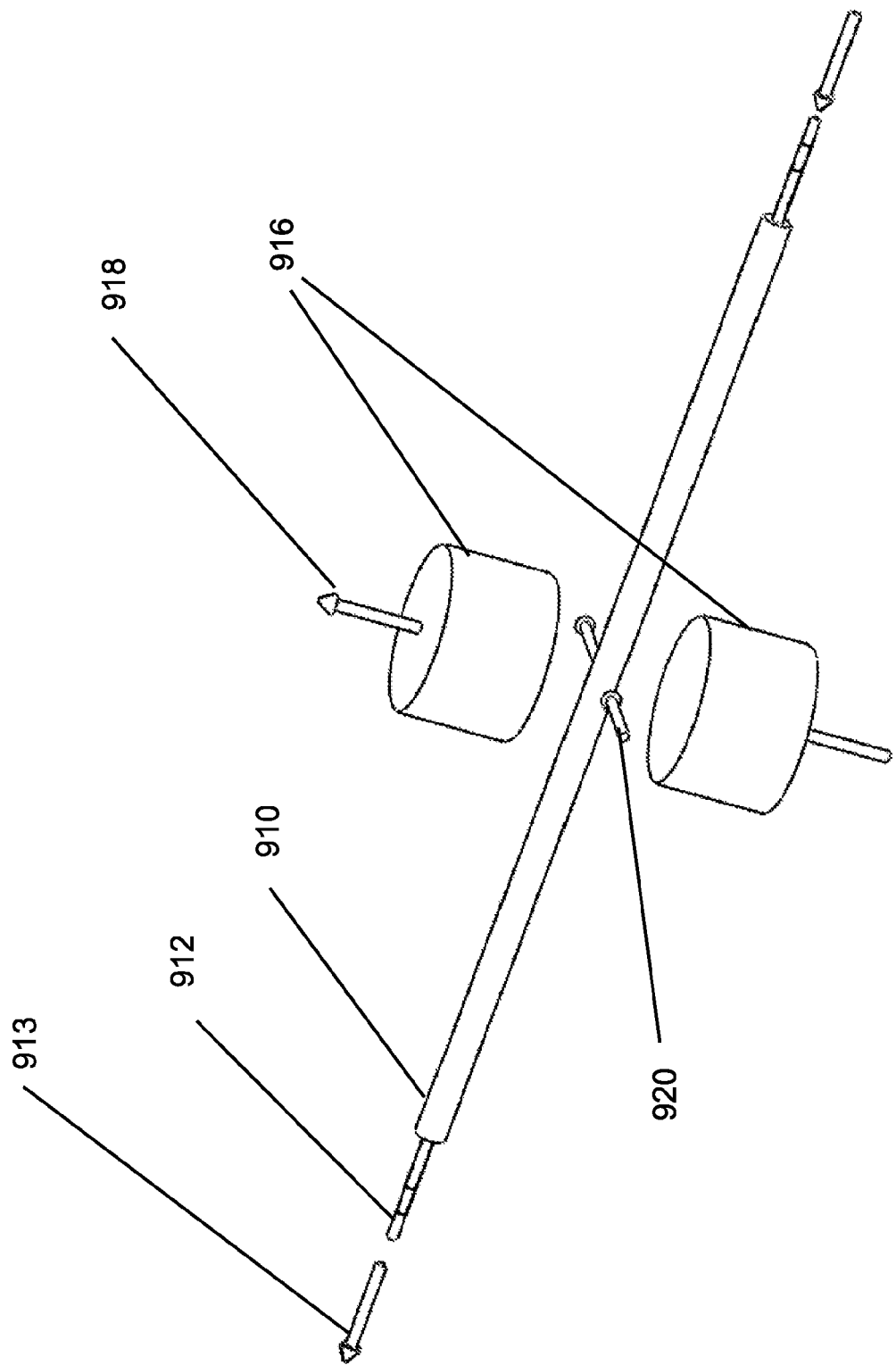
FIG. 13 shows the capillary tubes of the resonator of FIG. 12, without the rigid frame, and the force vectors produced by the current flow within the capillary tubes.

Various embodiments are shown in two drawings, a first drawing shows all of the elements, whereas a second drawing shows an outer frame removed, so that the inner elements can be viewed with greater clarity. Referring to FIGS. 12 and 13 a fluid properties sensor 908 includes capillary tube 910, which is disposed within a rigid frame 914, and fastened to the frame 914 at its ends, preferably by brazing or welding. Both the capillary tube 910 and the frame 914 are preferably composed of the same material, for example, type 316 stainless steel. Capillary tube 910 has a lateral resonant frequency, corresponding to a bending mode of the tube. At least one magnet 916 is mounted so that it has a field component perpendicular to the longitudinal axis of the capillary tube 910.

Capillary tube 912 is constructed in accordance to the generalized structure for a resonator 10, shown in FIG. 1. A transverse force can be exerted on the capillary tube 910 by means of an electrical conductor 912 (same as conductor 12 in resonator 10). A current (having direction indicated by arrows 913) passed through conductor 912 will interact with the transverse component of the magnetic field (indicated by arrow 918) so as to exert a Lorentz force (indicated by arrow 920 [viewed from the rear]) on the conductor 912, perpendicular to both the transverse magnetic field component 918 and the direction of current flow in the wire 913.

Conversely, if the capillary tube 910 and the conductor 912 contained within it move perpendicularly to the applied magnetic field 918, a current 913 will be induced in the conductor. This induced current 913 may be used to monitor the movement of the capillary tube 910.

Figure 14:
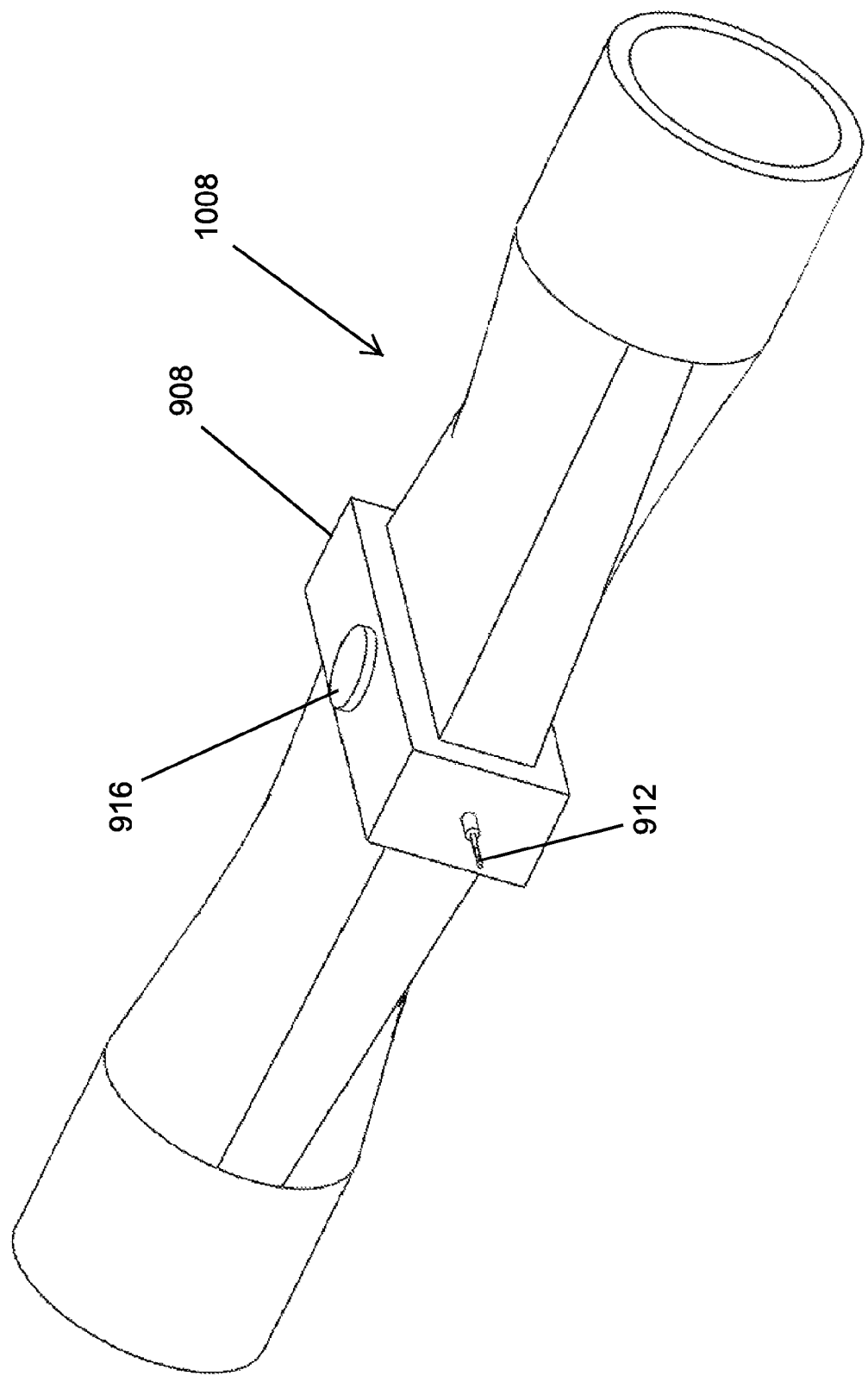
FIG. 14 shows the straight capillary resonant fluid properties sensor integrated into a flow channel.
Figure 15:
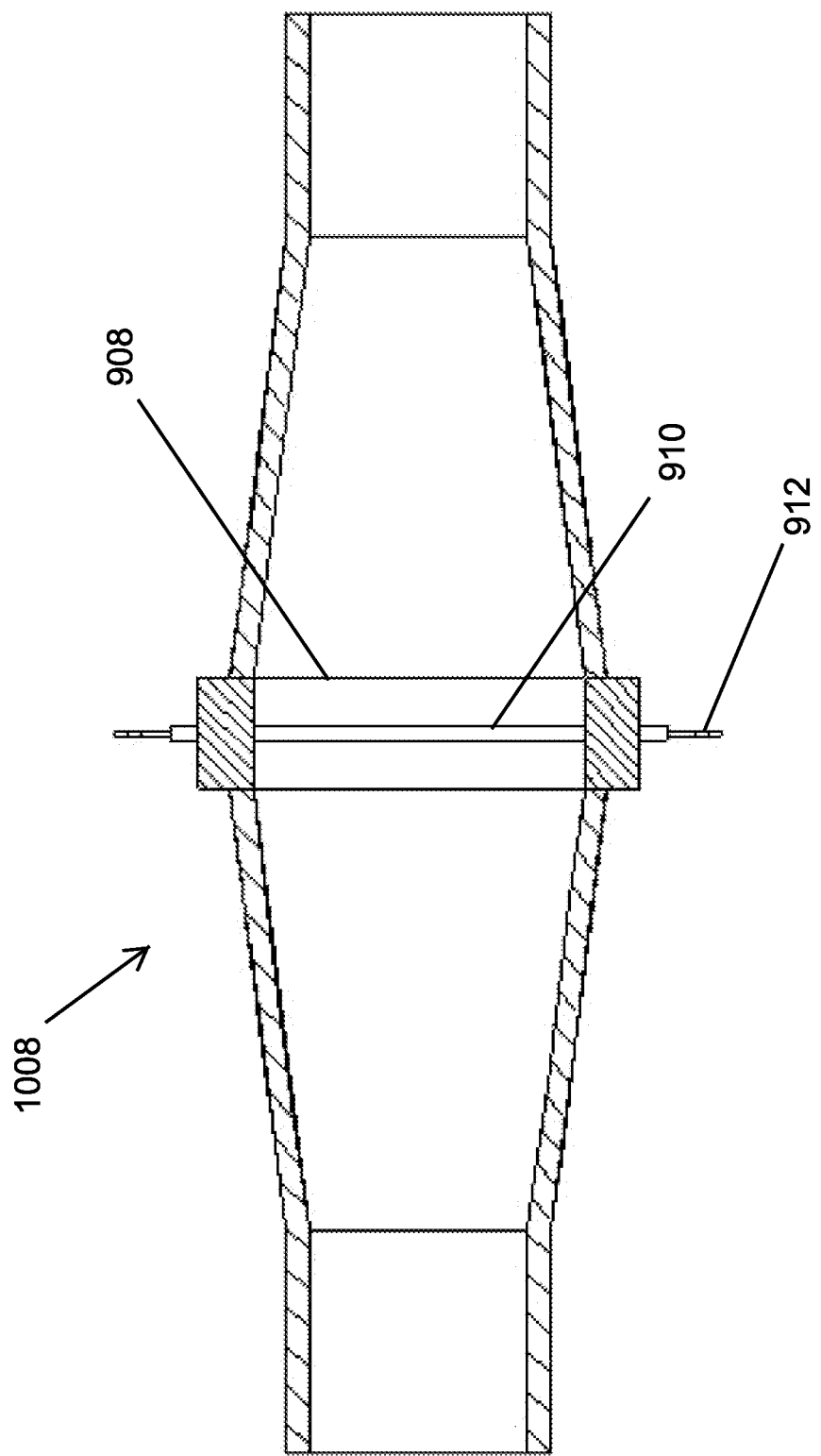
FIG. 15 is a sectional view of the sensor of FIG. 14.

In a typical application, the sensor is used to measure the viscosity and density of a fluid, downhole. Referring to FIGS. 13 and 14, a capillary sensor flow channel 1008 is shown, hosting capillary sensor 908, at its midpoint. Flow channel 1008 might be used in a downhole fluid sampling system.

It is known that an elastic cylinder moving perpendicularly to its own axis carries an "additional mass" of fluid with it, thus increasing its apparent mass and decreasing its resonant frequency, and that the shearing of the fluid near the cylinder's surface results in an energy loss that damps transverse motion of the rod.

A system similar to that disclosed in U.S. Pat. No. 8,291,750 can be used to both excite and measure the resonance of the capillary sensor, from which the fluid properties can be calculated. That system comprises a gated phase-locked loop that alternately excites and senses the motion of the resonator. It can be used to monitor both the resonant frequency and the damping of the resonator to determine the properties of the fluid in which it is immersed.

Other embodiments of the basic capillary resonator are possible, one of which is particularly advantageous. The sensor of FIG. 12 has a single element, whose vibration exerts a reaction force on the rigid frame in which it is mounted. When it is desired to measure fluids with very low viscosity, energy leakage from the resonator into the frame can be a significant source of error. Such energy leakage can increase the damping of the resonator to the point where it negatively impacts the accuracy of the measurement of damping due to the fluid.

In an alternative preferred embodiment of a fluid properties sensor 1108, energy leakage is minimized by arranging two identical resonant elements 1110A and 1110B in close proximity to one another, and sharing a common mounting frame 1114. As the current in 1110B will flow in opposite direction to current in 1110A, these two elements will vibrate in antiphase to one another.

In the embodiments described above, the capillary tube may be made of a non-magnetic material such as 316 austenitic stainless steel. It is advantageous to make the rigid frame of the same material as the capillary tubes so that the coefficients of thermal expansion of the capillaries and the frame are the same. In this way, as the temperature of the system changes, there is no change in the tension or compression experienced by the capillary tube(s). It is known that changing the axial force on a slender body vibrating transversely changes the resonant frequency of the body. As the temperature of the system changes, there is a corresponding change in the elastic properties of the capillaries. In order to compensate for the effect of temperature on the elastic behavior of the sensor, the resonant frequency of the capillary tube is measured as a function of temperature when the sensor is operating in air or in vacuum. This value can then be subtracted from the frequency of the capillary resonating in the fluid under test, giving a value for the net frequency change due to the density and viscosity of the fluid.

It is advantageous to measure the temperature of the capillary resonator in the immediate vicinity of the capillary. This can be done by measuring the resistance of the insulated conductor that runs through the lumen of the capillary. If the temperature coefficient of resistance of the wire is known, then its resistance at a particular temperature can be used to measure that temperature. This can be done, for instance, by measuring the ratio of voltage to current during the excitation phase of the operation of the sensor.

Although the above figures show embodiments in which the transverse magnetic field is supplied by permanent magnets, a portion or all of the bias field can be supplied by one or more electromagnets. This can be advantages in situations when there are magnetic particles in the fluid to be measured. If the bias field is supplied by permanent magnets, these particles may be extracted by the bias field and accumulate around the pole faces, perhaps physically touching the capillaries, or even blocking the flow channel. If, on the other hand, the bias field is provided by electromagnets, then the current to the bias magnets may be interrupted between measurements to allow accumulated magnetic particles to be swept away by the fluid flowing through the sensor.

Variations of the Resonator Configuration

Figure 18:
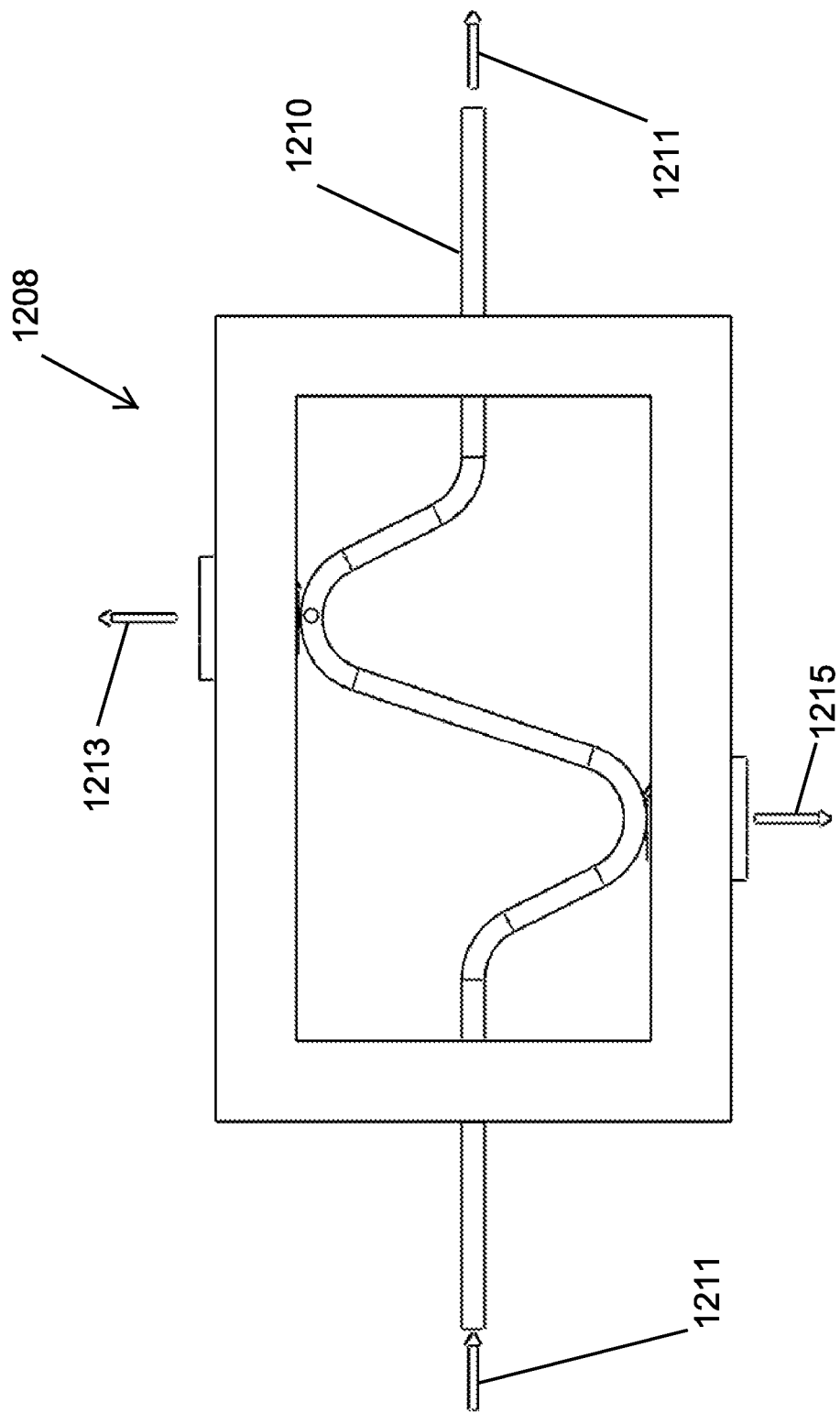
FIG. 18 shows the formation of the conductor-containing capillary tube into a serpentine curve.
Figure 19:
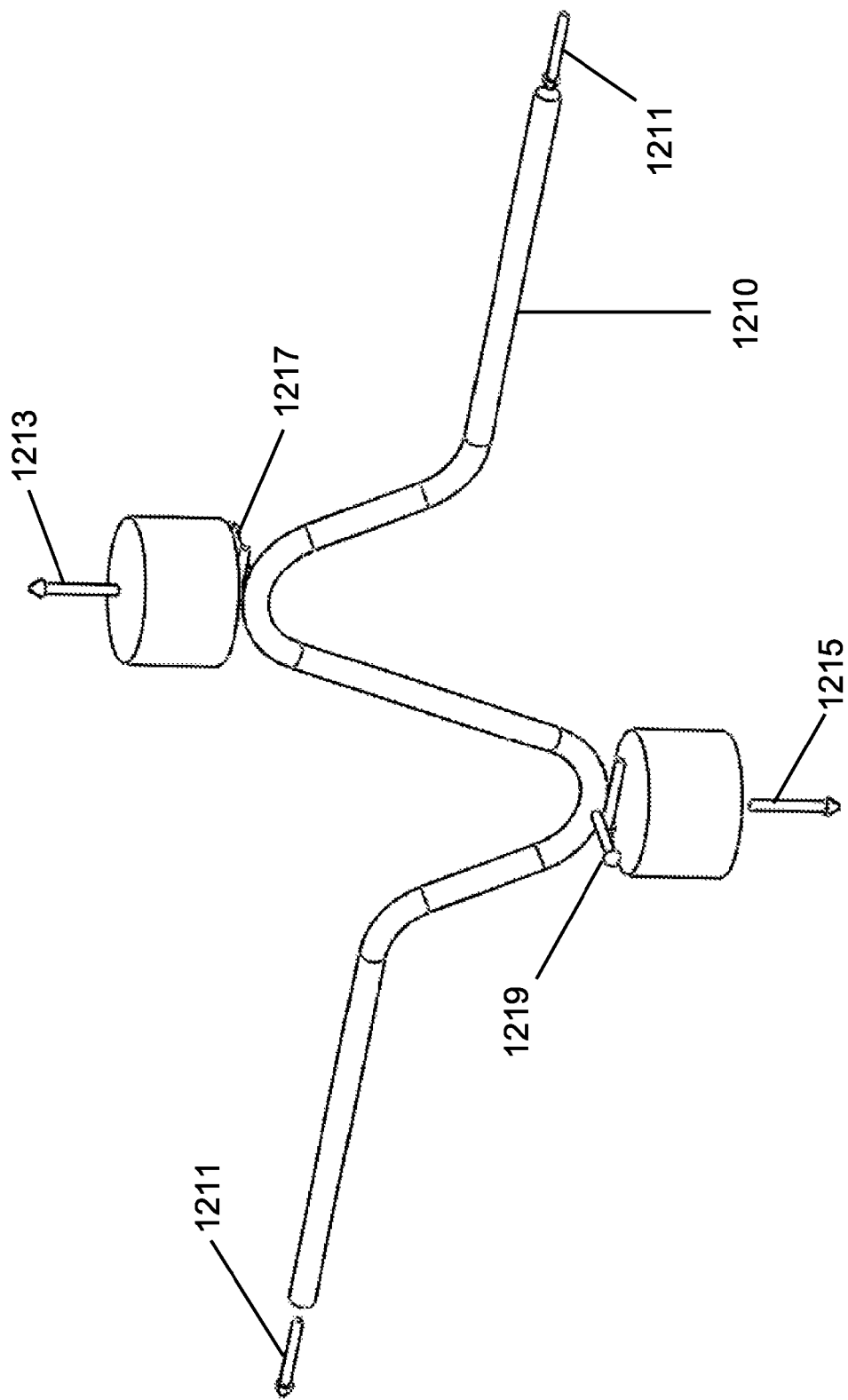
FIG. 19 shows the current, magnetic field and force vectors acting on the serpentine capillary.

Referring to FIGS. 18 and 19, in an additional preferred embodiment of a fluid properties sensor 1208, a capillary tube 1210, having identical internal construction to capillary system 10, is formed into a serpentine curve.

The arrows 1211 at the ends of the capillary show the direction of current flow. The capillary 1210 supplies the inertia and elasticity to determine the characteristics of the fluid in which the resonator is immersed, and the current to force and velocity to current transduction is carried out by the insulated conductor running through the lumen of the capillary. The arrows 1213 and 1215 above the serpentine curves of the capillary indicate the directions of the magnetic force vectors B1 and B2.

It can be seen that the forces F1 and F2 (having directions indicated by arrows 1217 and 1219) act in opposite directions, producing a torque around the axis coaxial with the straight sections of the capillary. The resonant frequency of this system is determined primarily by the torsional stiffness of the straight sections of capillary, which act as torsion springs, and the rotatory inertia of the loops of the serpentine capillary. When this resonator is immersed in fluid, the portion off the axis of the straight sections displace fluid normal to its surface, thereby increasing the apparent mass of the resonator, and causing a decrease in frequency dependent on the density of the fluid. At the same time, portions of the surface shear the fluid, resulting in an increase of the resonator's damping dependent on the product of viscosity and density, making its damping an indication of the viscosity-density product.

Figure 16:
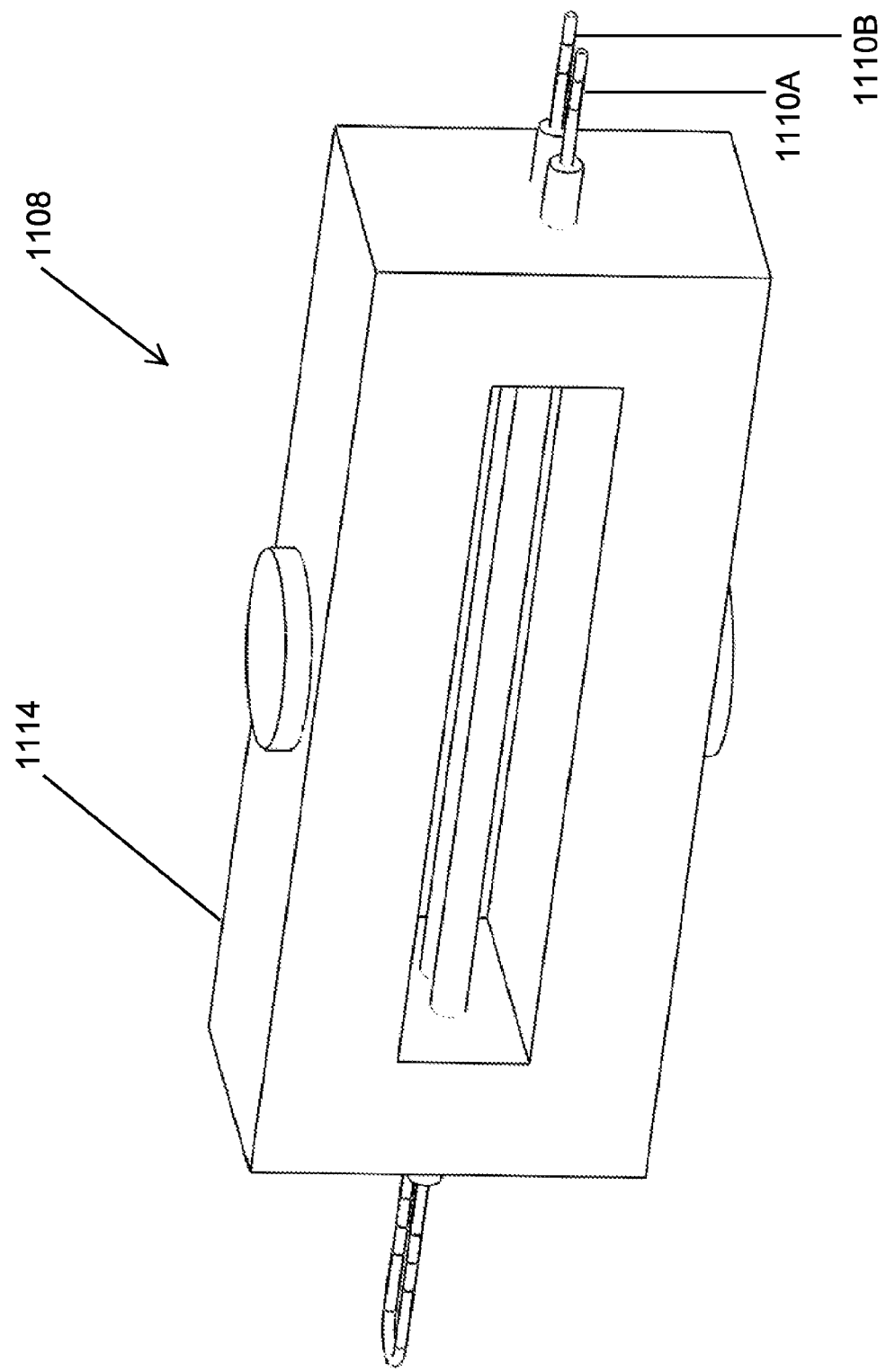
FIG. 16 shows a balanced resonant fluid properties sensor with two capillary elements within a common mounting frame.
Figure 17:
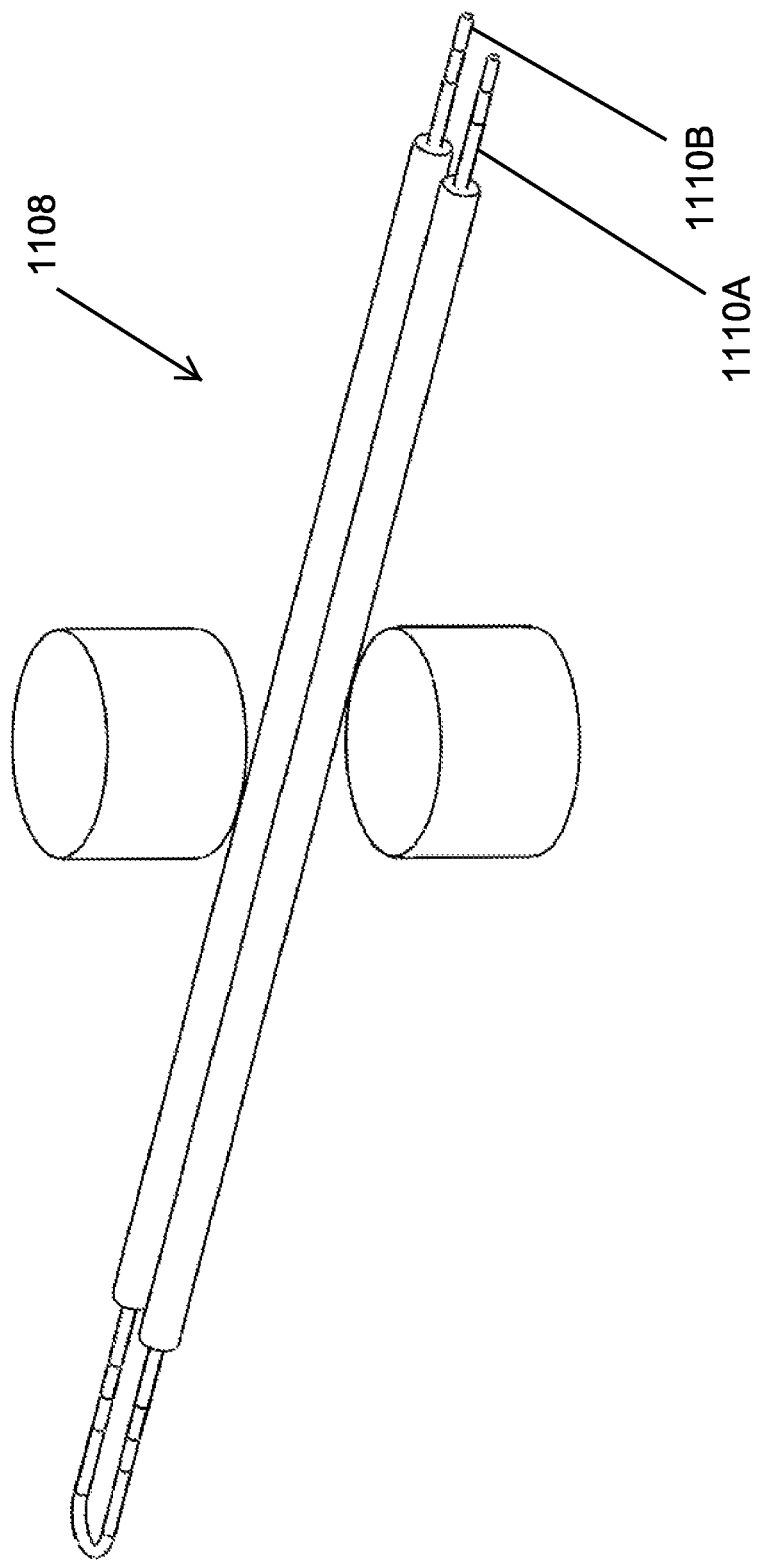
FIG. 17 is the resonant fluid properties sensor of FIG. 16 with the frame removed to show current flow direction, magnetic field vector, and forces on the capillary elements.
Figure 20:
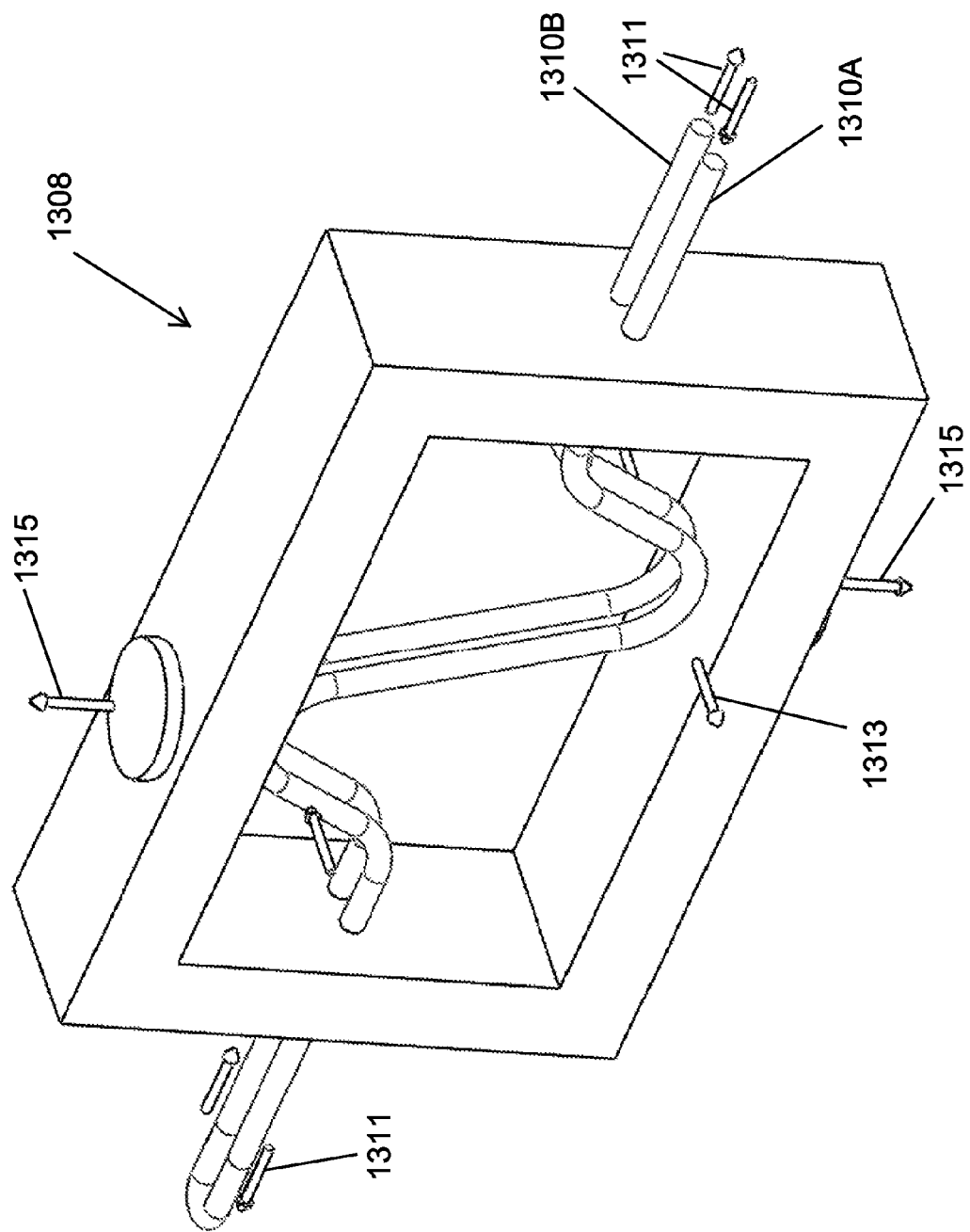
FIG. 20 is a balanced configuration of the serpentine resonant fluid properties sensor of FIG. 18.
Figure 21:
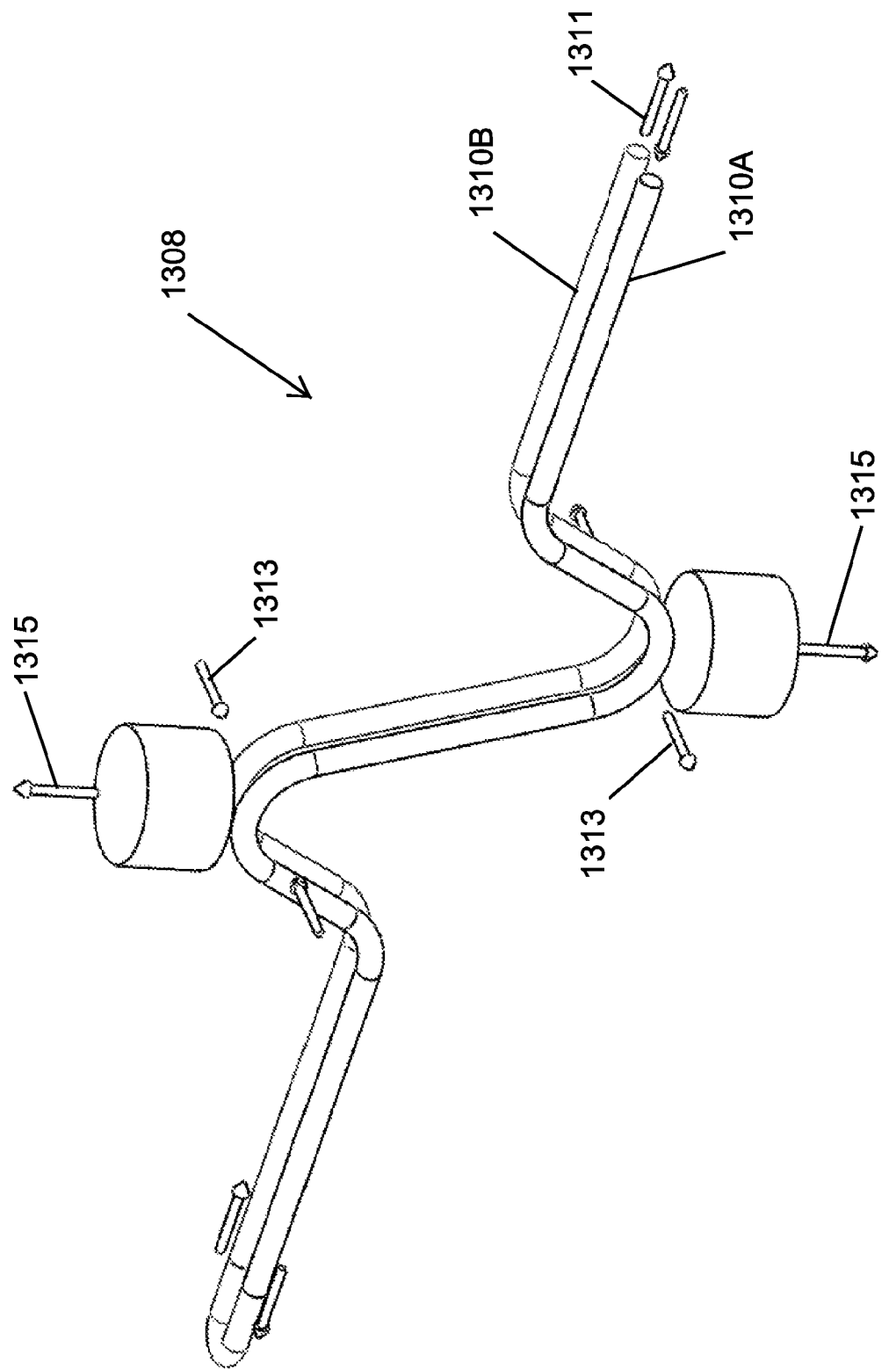
FIG. 21 shows the vector relationships among current, force, and magnetic field on the balanced serpentine resonant fluid properties sensor of FIG. 20.
Figure 22:
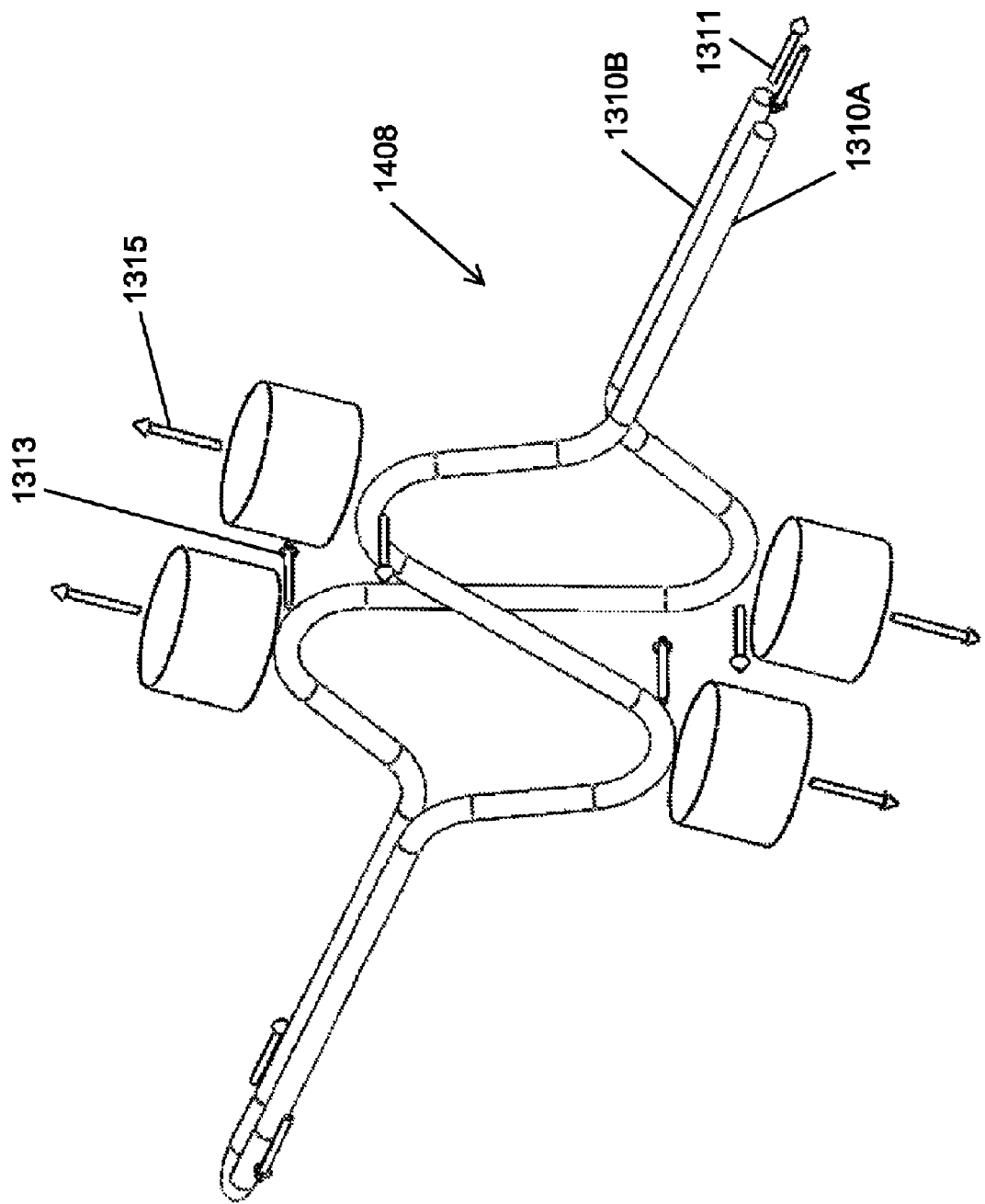
FIG. 22 is an alternative configuration of the balanced serpentine resonant fluid properties sensor of FIG. 20, but without the frame to show the force, magnetic field, and current flow vectors.

As in the case of the parallel straight sections of capillary disposed so as to balance mounting forces disclosed in FIGS. 16 and 17, serpentine resonators can also be arranged in a balanced configuration so as to minimize reaction forces on the mounting system. FIG. 20 below shows a preferred embodiment of a sensor 1308, having balanced serpentine resonators 1310A and 1310B. FIG. 21 shows the vector relationships among current 1311, force 1313, and magnetic field 1315 in sensor 1308. FIG. 22 shows an alternative preferred embodiment of sensor 1308.

Figure 23:
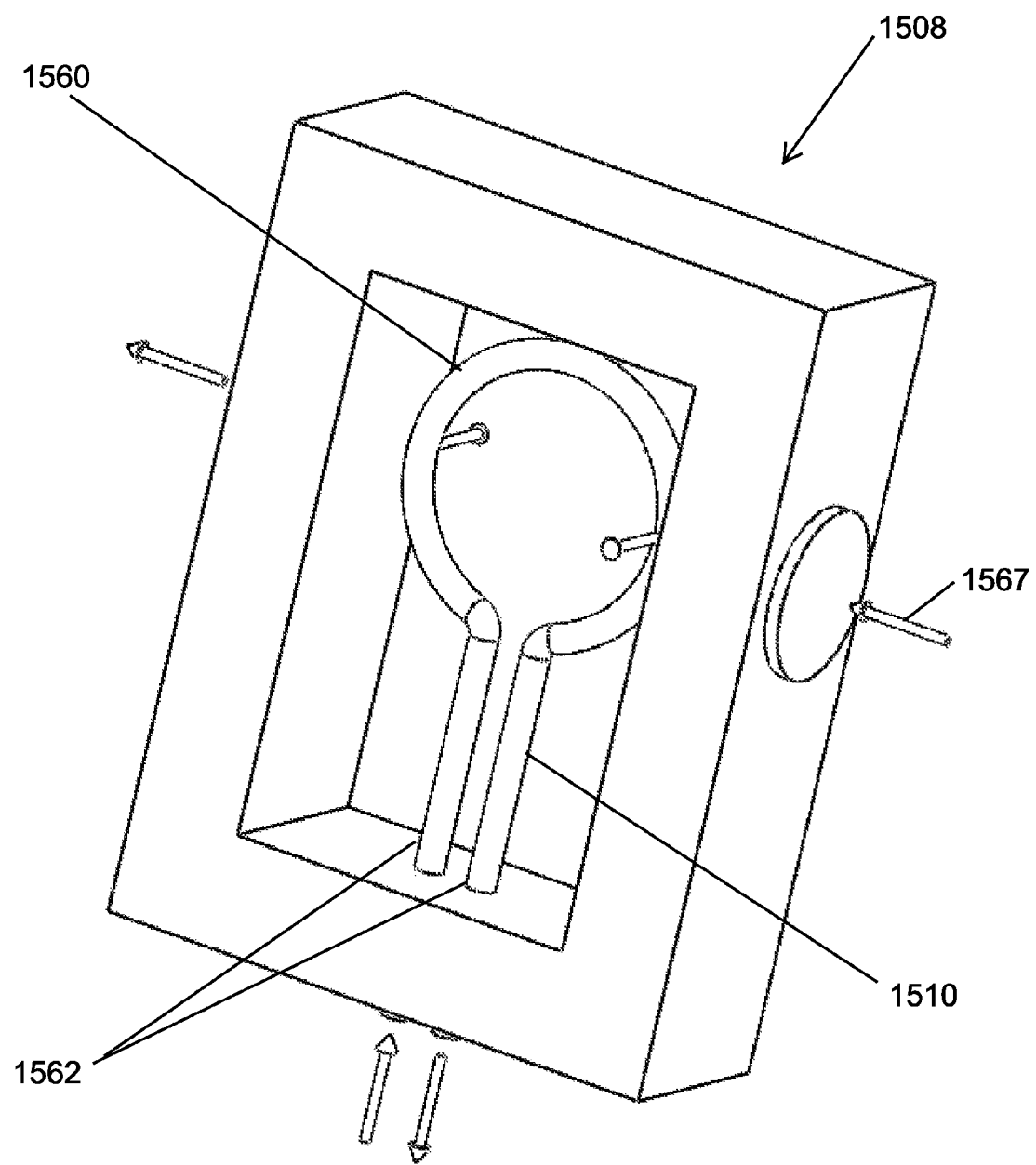
FIG. 23 shows another configuration of the capillary resonant fluid properties sensor with the capillary formed into a circular loop with legs.
Figure 23A:
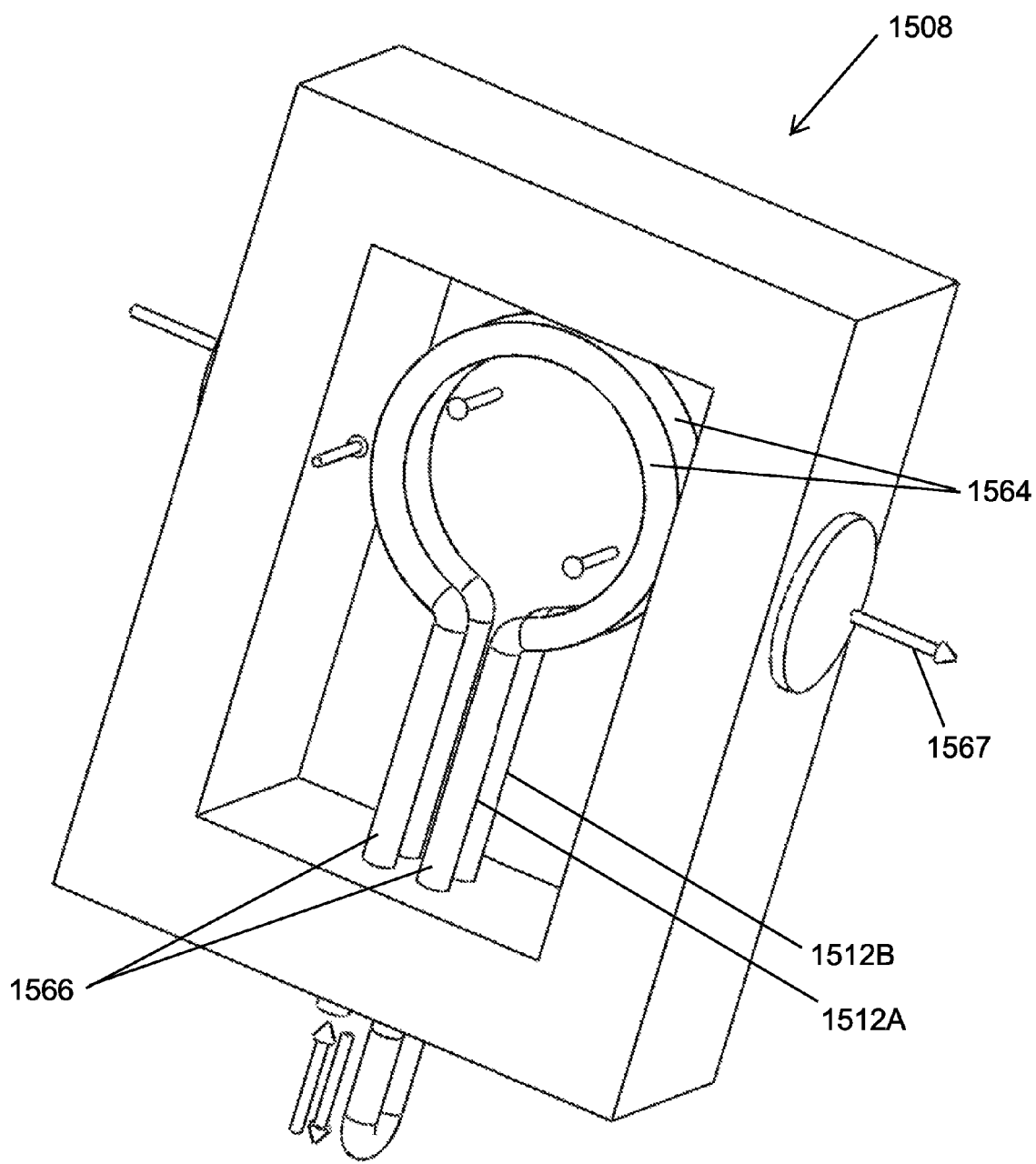
FIG. 23A is a balanced configuration of the capillary resonant fluid properties sensor of FIG. 23, with the capillary formed into circular loops with legs.
Figure 24:
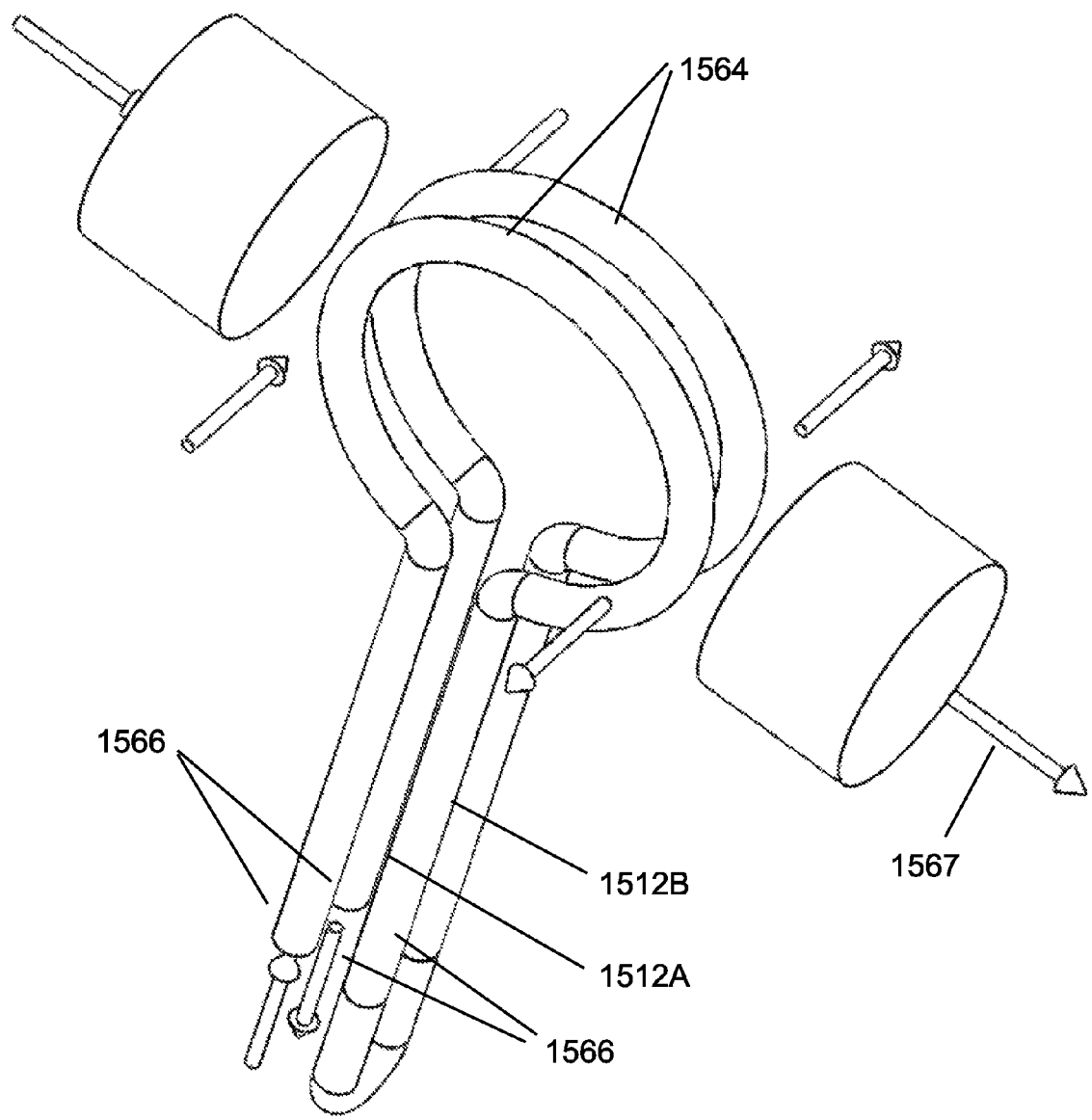
FIG. 24 is a balanced configuration of the round capillary loop sensor of FIG. 23 with the outer frame removed to show the force, magnetic field, and current flow vectors.

FIG. 23 shows a sensor 1508 with one resonator 1510 in which the capillary is formed into a circular loop 1560 with legs 1562. FIGS. 23A and 24 show a balanced arrangement of sensor 1508, having two resonators 1512A and 1512B, in which the capillary is formed into circular loops 1564 with legs 1566. The magnetic bias field 1567 is positioned parallel to the plane of the loops 1564, and perpendicular to its legs. Passing a current through the loops 1564 results in torsion of the loops 1564, causing them to vibrate in opposite directions, thereby forming a balanced resonance.

This configuration is similar to the U-shaped capillary resonator disclosed in U.S. provisional patent application 61/717,029, but has the advantage of offering a greater range of sensitivities to density and viscosity, as the rotatory inertia of the loop can be changed independently of the stiffness of the legs, which is not true of the U-shaped resonator.

Although specific vibrational modes are shown for each of the resonator configurations disclosed in this application, it is understood that each configuration may be driven in any of its resonant modes.

In addition, the configurations shown are indicative of certain preferred embodiments, but do not restrict the application of the method to a wide variety of other configurations. For instance, the serpentine resonant elements described above might also have more than two peaks and more than one inflection point, resulting in a larger surface area to increase its interaction with the fluid and hence its sensitivity.

The invention claimed is:

1. A resonant sensor for measuring properties of a fluid, comprising:
   (a) an elastic tube defining an interior volume and an interior surface;
   (b) a conductor extending through said interior volume;
   (c) solid material, present in said interior volume and joining said conductor to said elastic tube interior surface, so that force exerted on said conductor is directly transferred to said elastic tube; and
   (d) a magnet assembly that creates a magnetic field, thereby providing a Lorentz force on said conductor when a current is passed through said conductor.

2. The sensor of claim 1, wherein said elastic tube is electrically conductive and said solid material electrically insulates said conductor from said elastic tube.

3. The sensor of claim 2, wherein said solid material comprises insulation, covering said conductor, and hardened resin, filling any space between said insulation and said elastic tube interior surface.

4. The sensor of claim 1, further including a metal structure, defining a first aperture and a second aperture and wherein said elastic tube extends from said first aperture to said second aperture and is joined to said solid structure around said first aperture and around said second aperture, in a fluid impermeable manner.

5. The sensor of claim 4, wherein said elastic tube is in a U-Shape.

6. The sensor of claim 4, wherein said elastic tube is in the form of a letter "M" with rounded angles.

7. The sensor of claim 4, wherein said tubular element is attached to said solid structure around said first aperture and said second aperture by being welded to said solid structure around said first aperture and said second aperture.

8. The sensor of claim 4, wherein said metal structure is in the form of a base.

9. The sensor of claim 4, wherein said metal structure in the form of a frame.

10. The sensor of claim 1, further including a resistance measurement sensor being connected across said conductor, a resultant measurement of resistance providing a measure of the temperature of said sensor and said fluid surrounding said sensor.

11. The sensor of claim 10, wherein said current passed through said conductor is an alternating current, said alternating current having a frequency, producing an alternating voltage with said frequency across said resistance of said conductor, and wherein said resistance is measured by synchronous detection means synchronized with said frequency of said alternating current.

\* \* \* \* \*